United States Patent
Fritsch et al.

(10) Patent No.: US 7,144,486 B1
(45) Date of Patent: Dec. 5, 2006

(54) MULTILAYER MICROCAVITY DEVICES AND METHODS

(75) Inventors: Ingrid Fritsch, Fayetteville, AR (US); Charles Sherman Henry, Mississippi State, MS (US); Benjamin P. Bowen, Tempe, AZ (US); Walter R. Vandaveer, Lawrence, KS (US); Nicole Bratcher, Pittsburg, OK (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 248 days.

(21) Appl. No.: 10/020,776

(22) Filed: Dec. 12, 2001

Related U.S. Application Data

(63) Continuation-in-part of application No. 09/775,937, filed on Feb. 2, 2001, now abandoned, which is a continuation-in-part of application No. 09/255,950, filed on Feb. 23, 1999, now abandoned, application No. 10/020,776, which is a continuation-in-part of application No. 09/071,356, filed on Apr. 30, 1998, now abandoned.

(60) Provisional application No. 60/075,955, filed on Feb. 23, 1998, provisional application No. 60/055,527, filed on Aug. 8, 1997, provisional application No. 60/042,100, filed on Apr. 30, 1997.

(51) Int. Cl.
*G01N 27/31* (2006.01)
*G01N 27/327* (2006.01)
*G01N 27/333* (2006.01)

(52) U.S. Cl. .............................. 204/403.06; 204/403.1; 204/418; 204/400

(58) Field of Classification Search ........... 204/403.01, 204/403.03, 403.05, 403.06, 403.08, 403.13, 204/416, 418, 400
See application file for complete search history.

(56) References Cited

U.S. PATENT DOCUMENTS

| | | | |
|---|---|---|---|
| 4,225,410 A | * | 9/1980 | Pace ........................ 204/412 |
| 4,779,031 A | | 10/1988 | Arends et al. .............. 318/565 |
| 4,891,242 A | | 1/1990 | Ito et al. ..................... 427/53.1 |

(Continued)

FOREIGN PATENT DOCUMENTS

JP    03-176657 A   *   7/1991

(Continued)

OTHER PUBLICATIONS

JPO abstract of JP 04-215052 A.*

(Continued)

*Primary Examiner*—Alex Noguerola
(74) *Attorney, Agent, or Firm*—Head, Johnson & Kachigian

(57) ABSTRACT

Microcavities and micropores that are microscopic (<1 mm) in width and depth and contain any number of individually-addressable electrodes, separated by insulators, along the walls of each cavity. The conducting materials, and the insulator materials can be deposited alternately onto a starting substrate, which is typically an oxidized silicon wafer or polyimide film, but may be any substrate that shows good adhesion to the materials layered on it. The cavities are etched through these layers, perpendicular to the plane of the substrate, exposing the layers at their edges. Pores may be carved entirely through the device.

35 Claims, 10 Drawing Sheets

U.S. PATENT DOCUMENTS

| | | | |
|---|---|---|---|
| 4,961,806 A | 10/1990 | Gerrie et al. | 156/252 |
| 4,972,470 A | 11/1990 | Farago | 380/3 |
| 5,030,310 A | 7/1991 | Wogoman | 156/252 |
| 5,053,920 A | 10/1991 | Staffiere et al. | 361/383 |
| 5,066,372 A | 11/1991 | Weetall | 205/777.5 |
| 5,159,427 A | 10/1992 | Ogura et al. | 357/48 |
| 5,225,374 A * | 7/1993 | Fare et al. | 438/1 |
| 5,253,156 A | 10/1993 | Sakurai et al. | 363/98 |
| 5,290,420 A | 3/1994 | Matson | 204/403 |
| 5,313,150 A | 5/1994 | Arakawa et al. | 318/768 |
| 5,344,545 A | 9/1994 | Tsukada et al. | 204/415 |
| 5,355,301 A | 10/1994 | Saito et al. | 363/147 |
| 5,365,405 A | 11/1994 | Hoenlein et al. | 361/766 |
| 5,384,691 A | 1/1995 | Neugebauer et al. | 361/794 |
| 5,410,107 A | 4/1995 | Schaper | 174/255 |
| 5,412,558 A | 5/1995 | Sakurai et al. | 363/98 |
| 5,432,675 A | 7/1995 | Sorimachi et al. | 361/719 |
| 5,434,745 A | 7/1995 | Shokrgozar et al. | 361/735 |
| 5,437,999 A * | 8/1995 | Diebold et al. | 204/403.11 |
| 5,452,182 A | 9/1995 | Eichelberger et al. | 361/749 |
| 5,488,542 A | 1/1996 | Ito | 361/793 |
| 5,495,394 A | 2/1996 | Kornfeld et al. | 361/764 |
| 5,532,512 A | 7/1996 | Fillion et al. | 257/686 |
| 5,544,017 A | 8/1996 | Beilin et al. | 361/790 |
| 5,604,383 A | 2/1997 | Matsuzaki | 257/778 |
| 5,605,662 A | 2/1997 | Heller et al. | 422/68.1 |
| 5,608,192 A | 3/1997 | Moriizumi et al. | 174/255 |
| 5,608,617 A | 3/1997 | Morrison et al. | 363/147 |
| 5,616,888 A | 4/1997 | McLaughlin et al. | 174/260 |
| 5,619,108 A | 4/1997 | Komurasaki et al. | 318/140 |
| 5,629,559 A | 5/1997 | Miyahara | 257/666 |
| 5,629,574 A | 5/1997 | Cognetti et al. | 310/71 |
| 5,634,267 A | 6/1997 | Farnworth et al. | 29/840 |
| 5,641,944 A | 6/1997 | Wieloch et al. | 174/252 |
| 5,773,270 A * | 6/1998 | D'Orazio et al. | 204/403.01 |
| 5,820,551 A * | 10/1998 | Hill et al. | 204/403.04 |
| 5,846,814 A | 12/1998 | Galla et al. | 435/287.2 |
| 6,376,233 B1 * | 4/2002 | Wolf et al. | 435/288.4 |
| 2003/0085124 A1* | 5/2003 | Ufer | 204/400 |
| 2003/0106810 A1* | 6/2003 | Douglas et al. | 205/777.5 |

FOREIGN PATENT DOCUMENTS

| | | | |
|---|---|---|---|
| JP | 04-215052 A * | 8/1992 | |
| WO | WO 90/12314 A1 * | 10/1990 | |

OTHER PUBLICATIONS

English language translation of Urban et al. (WO 90/12314 A1).*
Wehmeyer et al. (Electroanalytical Properties of Band Electrodes of Submicrometer Width, Anal. Chem. 1985, 57, 1913-1916).*
Thormann et al. ("Voltammetre at Linear Gold and Platinum Microelectrode Arrays Produced by Lithographic techniques," Anal. Chem. 1985, 57, 2764-2770).*
Derwent abstract of JP 03-176657 A.*
*Stock Product Catalog 501. Baldor Motors and Drives. Jan. 1, 1997.
*The Animatics SmartMotor. Animatics Corporation.
*Industrial electronics. Technology 1998 Analysis & Forecast. IEEE Spectrum. Jan. 1998. p. 73-78.
*Craig D.T. Bratten, Peter H. Cobbold, Jonathan M. Cooper: Micromachining Sensors for Electrochemical Measurement in Subnanoliter Volumes: *Anal. Chem.*, 1997. vol. 69 No. 2, Jan. 15, 1997, pp. 253-258.
*K. Leyendecker, W. Bacher, W. Stark, A. Thommes: New Microelectrodes For the Investigation Of the Electroforming Of Liga Microstructures: *Electrochimica Acta*. 1994, vol. 39, No. 8 9, pp. 1139-1143.
*Osamu Niwa, Masao Morita, Hisao Tabei: Fabrication and characteristics of vertically separated interdigitated array electrodes: *J. Electroanal. Chem*. 1989. 267, pp. 291-297.
*Alan M. Bond, Darryl Luscombe, Keith B. Oldham, Cynthia G. Zoski: A Comparison Of the Chronoamperometric Response At Inlaid and Recessed Disc Microelectrodes: *J. Electroanal. Chem.*, 1988. 249, pp. 1-14.
*Thor D. Osborn, Paul Yager: Formation of Planar Solvent-Free Phospholipid Bilayers by Langmuir-Blodgett Transfer of Monolayers to Micromachined Apertures in Silicon: *Langmuir*. 1995, 11, pp. 8-12.
*Rose A. Clark, Paula Beyer Hietpas, Andrew G. Ewing: Electrochemical Analysis in Picoliter Microvials: *Anal Chem.*, 1997, 69. pp. 259-263.
*K.C. Burgers, K.J. Olejniczak. S.S. Ang. E. Porter: The Use of Multichip Module Technology for Power Electronics Miniaturization and Packaging: Department of Electrical Engineering. University of Arkansas: High Density Electronics Center (HiDEC). University of Arkansas. *Abstract*, 1997, pp. 35-41.

* cited by examiner

MULTILAYER MICROCAVITY DEVICES AND METHODS

CROSS-REFERENCE TO RELATED APPLICATIONS

This application is a continuation-in-part of U.S. patent application Ser. No. 09/775,937, filed Feb. 2, 2001, abandoned, which is a continuation-in-part of U.S. patent application Ser. No. 09/255,950 filed Feb. 23, 1999, abandoned, which claims priority from U.S. provisional patent application Ser. No. 60/075,955 filed Feb. 23, 1998. This application also claims priority from U.S. provisional application Ser. No. 60/055,527, filed Aug. 8, 1997, and is also a continuation-in-part of U.S. patent application Ser. No. 09/071,356, filed Apr. 30, 1998, abandoned, which claims priority from U.S. provisional application Ser. No. 60/042,100, filed Apr. 30, 1997. Each of these applications is hereby incorporated by reference.

BACKGROUND OF THE INVENTION

1. Field of the Invention

The present invention relates to microelectrodes fabricated in microcavities being capable of both detecting and performing electrochemical reactions and methods for manufacturing microelectrodes inside microfabricated cavities. The invention also relates to such microcavities whose openings have been covered by a thin film or membrane. The invention also relates to microelectrodes in microfabricated pores.

2. Prior Art

Electrochemistry has proven to be a valuable tool for the research, production and detection of chemical compounds and the reactions that produce them. Electrochemical cells can be used to detect the presence of a wide variety of compounds dissolved in water, organic solvents and even gases. They may also be used to monitor and facilitate a variety of chemical reactions, especially oxidations and reductions. For the past several years, there has been a desire to miniaturize electrochemical cells. This is motivated by the cost, availability and toxicity of the samples tested or monitored as well as that of the materials used to make the cells. This has led to a new technical field that revolves around microelectrodes and the search for three dimensional structures that optimize their performance. Especially desirous structures are individually addressable compartments that would comprise miniature, complete electrochemical cells in which reactions may be performed and monitored. Cavities in inorganic materials have been constructed to this end.

Microelectrodes have several advantageous properties over conventional electrodes. Because of their small area, double layer capacitance is reduced relative to that of electrodes of conventional size. This permits faradaic current to be measured and distinguished from charging current on a submicrosecond time scale. Due to smaller electrode dimensions, the current i is smaller, and therefore iR drop is smaller, where R is uncompensated resistance, allowing measurements in resistive media. In addition, faradaic processes at microelectrodes can be time-independent due to steady state diffusion at sufficient time scales, and this characteristic is useful in sensor applications. Microelectrode geometries that have been reported include hemispheres, disks, bands, tubes, rings, and cylinders where one or more geometrical dimension is typically of the order of 1 to 20 µm.

A number of obstacles must be overcome to build microelectrochemical sensing devices. Many problems are associated with the materials used to make and modify them. These include how to place materials in microscopic locations with precision, how to stabilize these materials under electrochemical conditions, how to control the reactions that cause instability, and how selectivity can be introduced for electrochemical sensing purposes.

In general, small inorganic and organic microstructures can be constructed by several methods. For example, features have been fabricated at the micron level using optical lithography (microfabrication). More recently, structures only a few Angstroms in diameter have been constructed without lithography. Unfortunately, such an approach does not address formation of small cavities or placement of probes, such as electrodes, both inside and outside so that both compartments on either side of the film can be analyzed.

Microelectrodes in microfabricated cavities appeared as early as 1983 in work done by Osteryoung and Hepel. The main advantage of these types of electrodes is their ability to isolate the working electrode from convective fluxes in a bulk solution. They reduce noise in amperometric detection by eliminating current variations caused by random convection fluctuations. Microelectrodes have been used in complex media such as blood and urine, and have been used to provide spatially-resolved information from surfaces and cell membranes.

Despite the advantages of microelectrodes, progress has been impaired by difficulty in constructing electrodes with dimensions smaller than 1 µm. Band electrodes with widths less than 1 µm have been constructed using conductor foils. Metal vapor deposition has been used in some cases to make band electrodes with a width in the range 20–200 nm. Typically, band electrodes were then constructed by grinding the edges with sand paper or alumina. The grinding process has been shown to be less reproducible and leads to significantly smaller limiting currents. Much less work has been done in combining the use of metal vapor deposition and conventional photolithographic and etching techniques to make microelectrodes. Nylander and coworkers reported fabrication of an electrode array with 200 nm-wide electrodes using these methods. However, the electrodes on the array were not independently addressable.

Several researchers have also attempted to miniaturize complete electrochemical cells. With proper design of the substrate, the volume of sample required for the analysis would be minimized. This is important because of the necessity to minimize the sample volumes when dealing with toxic waste or precious body fluids or expensive reagents or substances like DNA. The volume of their cells are typically in the µL range. It is desirable, however, to create electrochemical cells that are substantially smaller. Cells having volumes in the pL or fL range, one billionth to one millionth the size of a µL, constitute a substantial improvement over existing technology.

When constructing extremely small electrochemical cells, it is often desirable for their microfabricated features to allow a film or membrane to be assembled across the structures and between two compartments that house the sample solutions or gases. One way in which to do this is to construct cavities or wells within an inorganic or organic substrate and bridge thin films across them.

Thin film membranes that form a barrier between gases or fluids are important to many natural and industrial processes. They range from separations of gas or liquid mixtures with polymeric membranes to communication between cells across cellular membranes. In some examples, thin film membranes serve as barriers for some chemical compounds and are permeable for others. These films can be supported on the edges or throughout the structure for strength. A large range of thin film materials have been studied and they exhibit a wide variety of properties. These materials serve well in applications of analytical separations and chemical analysis. However, because they are extremely thin, they are flimsy and tear easily unless they are well supported.

There is a drive in analytical chemistry toward miniaturization of methods of chemical analysis and the development of devices that provide multiple analyses simultaneously. An array of thin films, suspended across openings in a substrate that probes each independently would have far-reaching applications in many fields of science. A significant advantage of miniaturization is that the thin film membranes should become more stable, as distance between support structures decreases. However, two major problems that are inherent in constructing such a device are the need for a high degree of control over spatial distribution of the materials and a means by which to probe the array. Until recently, free-standing thin films have been supported by bulk, porous materials or on the edges of a single opening between compartments of gases or fluids.

The ability to miniaturize devices for the purposes of chemical analysis requires designing materials on a small scale and connecting these materials to instruments that can monitor their response to a stimulus. Established processes to pattern materials on a micron scale are found in the silicon industry, and are given the generic name of microfabrication. Almost all the materials patterned in this way are inorganic. However, materials that are most valuable for chemical analysis are organic molecules which can have a highly specific function and whose structure can be altered to modify that function in subtle ways. Many organic molecules that demonstrate specialized function are naturally formed in biological membranes. Thus, to develop capabilities of miniaturized chemical analysis for the next decade, it is of utmost importance to understand how to interface biological membrane-like materials with microfabricated inorganic materials.

The use of biologically-important molecules for immuno- and bio-sensors is of interest because they impart selectivity for a large variety of analytes. Many of these molecules reside naturally in cellular membranes. There are existing techniques that use microelectrodes and microelectrode arrays that are coated with films of materials that are of interest in chemical sensing. Traditionally, biologically important molecules are covalently attached to the surface of an electrode or incorporated within polymers. Thus, networks of molecules are created in two-dimensions across the surface of the electrode. Disadvantages include denaturation of the molecules due to the attachment procedure, difficulties in controlling the environment around the molecules either because the molecules are directly on the surface or because the surrounding molecular network is not very well ordered, and a lack of reliability in the results due to the proximity of the membrane and the electrode. In these systems, the electrodes are placed immediately adjacent to the film. Because the solid substrate with electrodes attached to one side of the film, diffusion of species completely through it is blocked. There is also the problem of the effect of the substrate on the properties of the film and the permeability of the film. These significant problems call into serious question the accuracy of measurements obtained using these techniques. It is highly desirable to find a method that would allow the electrodes to remain within extremely close proximity of a membrane in order to maintain fast time scales in detecting diffusing species, while at the same time not coming into actual contact with the membrane. This would allow the membrane and its constituents to behave more naturally, and result in more accurate and more reliable measurements of molecular diffusion or transport.

Polymers and bi-layer lipid membranes (BLMs) have been used in conjunction with electrochemical sensors for many years. BLMs have been used previously by Osborn and Yager in an application similar to the ones described above. In that report, the design consists of only a single Ag/AgCl reference electrode fabricated onto a glass microscope slide and then fused to etched silicon. This limits the analytical applications to systems that exhibit a change in the conductance through the membrane.

There are three primary ways to construct planar bi-layers across openings. They are known as the pinhole, the patch-clamp pipet tip, and the quartz/amphiphile sandwich techniques. In the first, bi-layers are assembled by painting amphophilic molecules across a hole which is typically several microns in diameter in a hydrophobic (Teflon) barrier between two chambers holding aqueous solutions. In the second method, a Langmuir-Blodgett technique is used: a glass pipet tip is lowered and then removed from a Langmuir monolayer at an air/water interface. Both configurations allow determination of conductivity through the bi-layers. In the third approach, lipids are sandwiched between two quartz plates, with a gap that is 10's of Angstroms wide. Molecules are aligned according to the pretreatment of the inner quartz surfaces. The first two tools pose two significant disadvantages; the pinhole or pipet tip is too small for convenient spectroscopic analysis and the distance between membrane and electrodes (for conductivity measurements) is limited to large values (millimeters or greater). In both cases, electrodes on either side of the bi-layer are macroscopic in size an cannot be positioned close enough to the bi-layers to monitor diffusion. In fact, these techniques only monitor capacitance of the bi-layers or changes in conductivity of ions through them, where electrodes do not need to be located adjacent to the bi-layers. They are incapable of accurately measuring diffusion or transport across the membranes. The quartz/amphiphile sandwich is easily accessible spectroscopically (by circular dichroism and X-ray scattering). However, it is not useful for studies of assembly dynamics or conductivity measurements. It is therefore desirable to develop a method for measuring the electrochemistry extremely close to the membrane, ideally in an environment conducive to spectroscopic analysis as well.

Diffusion, transport and membrane fusion are important in understanding the placement and function of newly synthesized membrane constituents, the pathway of conduction of nerve impulses, cellular metabolism and infection of cells by viruses and microorganisms. Fusion has been studied using fluorescing molecules and model vesicles. One can use fluorescence to allow mixing of the molecules into the membranes (via fluorescent-tagged lipids) and leakage out of vesicles (via fluorescein) during fusion. Active transport has also been studied indirectly by measuring ATPase activity of transport proteins. However, a method to corroborate these studies and perform these measurements in more accurate ways is highly desirable. Microcavities containing electrodes traversed by a BLM could provide such a method.

Microencapsulation methods are of interest in pharmaceutical, agricultural, adhesive, flavor and fragrance, and ink technologies. The current application most similar to the invention described herein is microencapsulation of chemicals in liposomes. A problem with most encapsulants is the limited control available for dispensing the contents. Often the coating of the capsule regulates the extent of dispensing of the internal components. It is desirable to construct microcapsules that can be reliably activated to release their contents.

SUMMARY OF THE INVENTION

The present invention includes several constructed devices that contain cavities or similar structures that are microscopic (<1 mm) in width and depth and contain any number of individually-addressable electrodes, separated by insulators, along the walls of each cavity.

The conducting materials, for the electrodes and the insulator materials can be deposited alternately onto the starting substrate, which is typically an oxidized silicon wafer but may be any substrate susceptible to any layering process that allows deposition of additional layers of materials, such as thermal evaporation, electron beam evaporation, sputtering deposition, spin coating, molecular beam epitaxy or the like. Photolithography and layering processes can be combined and used to deposit alternating insulating and conducting layers onto a substrate to form a surface for subsequent microcavity formation. While these methods are well known to those skilled in the art of microfabrication, combining these methods to form microcavities having independently addressable microelectrodes is a novel idea that has not been done before.

The cavities are then etched through these layers, perpendicular to the plane of the substrate, exposing the layers at the cavity edges. Each cavity may hold as little as a few femtoliters in volume. The bottom of a cavity have a selected number of electrodes or have a microfabricated-patterned electrodes housed therein. Alternatively, the cavities may be altered by placing a hole in the bottom of the cavity to form a pore which penetrates entirely through the device.

Any of the electrodes in the cavities or pores may be modified and used as reference electrodes or working electrodes, allowing complete electrochemical experiments to be performed within the cavity.

The cavities also offer some protection from convection currents in surrounding solution. For example, the top surface surrounding a cavity may be modified to enhance or diminish assembly of thin film materials across the cavity. These thin film materials may be polymers or assemblies of molecules such as phospholipid bi-layers or bi-layer lipid membranes (BLMs) that eliminate or control access of other species into and out of the cavity.

In one exemplary embodiment the fabrication of recessed microdisk electrodes (RDMs) and microcavities is accomplished by forming a hole through a gold (Au) and polyimide layer exposing an underlying Au disk. The top layer of Au, while not used in the electrochemical measurements is essential in the fabrication process so that cavities with well-defined, vertical walls can be produced. Cavity devices that accommodate two individually-addressable electrodes have been described elsewhere and so the present invention uses the same design for a more simplified electrode configuration.

In one exemplary embodiment, the fabrication of RDMs includes four steps. A 2 μm silicon dioxide ($SiO_2$) film is grown on a silicon (Si) wafer by thermal oxidation. The wafer is spin-coated with positive photoresist and exposed to ultraviolet (UV) light (400 W, 300 nm) through a photolithographic mask (HTA Photomask). The photoresist is developed, leaving a pattern of a series of parallel lines, which eventually become the contact leads and microdisk electrodes. A 15 Å (Cr) film, which serves as an adhesion layer, and 1000 Å gold (Au) layer are deposited on the photoresist by thermal evaporation (Edwards 306 Auto). The wafer is sonicated for 15 min in acetone, which dissolves the photoresist, causing lift-off of the metal on top.

After drying for 30 min at 125° C., the wafer is spin-coated with polyimide (4 μm thick). The polyimide is polymerized by exposure to UV light and then cured at 150° C. for 30 min and 250° C. for 30 min to cross-link the polymer. The layers of Cr (15 Å) and Au (1000 Å) are then deposited on top of the polyimide by thermal evaporation. The wafer is spincoated with positive photoresist. The photoresist is patterned by UV-exposure through a second photolithographic mask (HTA Photomask). The Au and Cr layers are etched simultaneously with 50% aqua regia (1 $HNO_3$:3 HCl). The remaining photoresist is stripped with acetone and the wafer is dried for 30 min at 125° C. This leaves a layer of Au/Cr covering the electrode lines with an area over the end of the lines left open for contact purposes.

The wafer is then spin-coated with photoresist and patterned using a third photolithographic mask (Photronics). This step leaves a circular opening through the photoresist over each region defined by the lines in the first gold layer. The topmost layer of Au is etched using radio frequency (RF) sputtering (5 min, 50 sccm Ar, 30 mT, 500 V). The polyimide is etched with reactive ion etching (RIE) (13 min, 40 sccm $O_2$, 10 sccm SF, 300 mT, 300 W). Before use, the electrodes are cleaned by sonicating in acetone for 30 s.

In another exemplary embodiment of the invention, microcavities may be formed in a similar way. The fabrication of microcavity electrode arrays is accomplished through the use of photolithographic techniques developed for integrated circuit technology. One exemplary cavity includes 5 primary layers of material. Layers 1, 3, and 5 are gold, with a chromium adhesion layer, while layers 2 and 4 are an insulative polyimide. Layers 1 and 3 serve as the microdisk and nanoband electrodes, respectively. Layer 5 helps maintain the definition of the cavity and prevent tapering during the etching steps. The arrays are generated by depositing and patterning each layer of conductor and insulator. This generates a set of contact lines separated by a sheet of insulator for each electrode. The last step in the fabrication is to create the cavities and expose the microelectrodes using dry etching procedures. Details of fabrication for each layer are listed below.

Layer 1. Both sides of a single crystal silicon wafer are coated with 3 μm of $SiO_2$ at 250° C. by plasma enhanced chemical vapor deposition (PECVD, Plasmatherm, System VII). Alternatively, the $SiO_2$ could be grown on the wafer by thermal oxidation at 650° C. for 8 hours. This serves as an initial passivation layer between the electrodes and semi-conductive silicon wafer. Layer 1 is patterned using a lift-off procedure that leaves the appropriate pattern.

Layers 2 and 4. Wafers are spin-coated with photo-sensitive polyimide (4 μm). The polyimide film is exposed to 350 nm UV light for 12 s through a Karl Suss MA-150 mask aligner to cross-link the polymer leaving a continuous, defect free insulator film. The polyimide is cured at 150° C. for 30 min, followed by 250° C. for 30 min. The wafer is allowed to cool to room temperature before the fabrication continued.

Layer 3. 15 Å Cr and 500 Å Au are deposited by thermal evaporation. The Au thickness of this layer determines the width (w) of the tubular nanoband electrode. The wafer is spin-coated with 4 μm of photoresist. The photoresist is patterned by exposure through a second Cr mask. The Au and Cr are etched simultaneously in 50% aqua regia (3 HCl: 1 HNO$_3$: 4H$_2$0). The absence of the ultra-thin Cr layer is verified through resistance measurements with a multimeter. The remaining photoresist is stripped with acetone after the Cr/Au layer had been etched. After rinsing, the wafer is dried for 30 min at 125° C. prior to coating with polyimide.

Layer 5. A top layer of Au is essential to producing cavities with well-defined, vertical walls. Thermal evaporation is used to deposit 25 Å Cr and 1500 Å Au. Photoresist is deposited and patterned according to the procedure for layer 3 using a third Cr mask. The Au and Cr are etched with aqua regia as described above. The remaining photoresist is removed with acetone and the wafer rinsed thoroughly with deionized water.

Cavities are created using standard dry etching procedures. The substrate or wafer is spin-coated with photoresist (6 μm). The photoresist is patterned by exposure to UV light through a fourth Cr mask. Layer 5 is etched with RF Ar$^+$ sputtering for 5 min and layer 3 for 2 min using a 500 V DC potential with constant pressure (30 mT) and flow (50 sccm) of Ar. The polyimide is etched using reactive ion etching (RIE) with a mixture of O$_2$ (36 sccm) and SF$_6$ (4 sccm) at 300 mT and 300 W RF power for 13 min.

There is a tendency for layers to partially diffuse into adjacent layers. On larger scales this type of diffusion is insignificant. However, because of the extremely small scale of these microcavities, this diffusion can substantially reduce the quality of the microelectrodes. When A extremely thin layers are desired, compounds which inhibit diffusion are preferable for the adhesion layers. It is also sometimes beneficial to incorporate adhesion layers that inhibit diffusion between conducting and insulating layers.

The initial layer of silicate is not necessary when glass is used as the substrate. When silicon is the substrate, only a very thin coating, 2–3 micrometers thick, is required. For other substrates, different initial coatings of different thicknesses may be required depending on the what chemicals are used for the adhesion layer and the photoresist employed.

Gold and copper are typically used for the conducting layers. However, any chemical that may be applied to a substrate by any process that allows deposition of additional layers of materials, (thermal evaporation, electron beam evaporation, sputtering deposition, spin coating, molecular beam epitaxy or the like) and has good conducting qualities may be used. Those skilled in the art of electrochemistry will appreciate that different conducting compounds or elements will be preferred for different applications of the invention. The deposited conducting layers may be extremely thin, less than 100 angstroms (Å) thick. This is the minimum required to adequately conduct an electric current. Although the conducting layers may be as thick as desired, many of the advantages of the invention lie in its microscopic size.

The insulating layers are also extremely thin, less than 3000 angstroms (Å) thick. It is often desirable to form thicker insulating layers. The thicker the insulating layer, the less capacitance there is between the electrodes. Capacitance between the layered electrodes necessitates higher voltage, and can increase noise. However, it is sometimes beneficial to increase the capacitance in some applications of the invention, such as where chemical changes caused by a changing electromagnetic field are being measured. Three materials, photosensitive polyimide, SiO$_2$ and Si$_3$N$_4$ are specifically mentioned in the exemplary embodiments of the invention. However, any compound that adequately insulates the conducting layers it is sandwiched between may be used.

The final layer is a conducting layer. The reason for this is that a top layer creates a better defined rim on the cavity. However, an insulator or any other desirable material capable of retaining well defined vertical walls would be suitable for a top layer as an alternative.

Photolithography may also be employed to alter the geometry of a RDM located at the bottom of a microcavity. Instead of being the same shape as the cavity, the microelectrode at the bottom of the well may be linear, stretching across the diameter of the cavity. It may also be designed to only cover one half of the bottom of the well. Any number of patterns may be used for the microelectrode at the base of the cavity by simply modifying the mask used during photolithography of the first layer.

In other exemplary embodiments, structures other than microcavities are discussed. For example, micropores may be created in addition to microcavities. Multiple electrodes can be fabricated in arrays of micropores using the alternating layer method. An advantage of having two or more electrodes within the same small region is for the purpose of performing self-contained electrochemical analysis on small samples. Construction of microcavities often follows microfabrication techniques which involve many steps and sophisticated masks, but construction of micropores in a flexible polyimide substrate can involve a low-technology approach at a reduced cost.

Amino acid analysis in alkaline solutions was demonstrated with a microcavity device with a copper tubular nanoband (TNB) electrode. The self-contained electrochemistry at the microcavity devices allows the analysis of small volumes in flowing solutions for amino acid detection. In some exemplary embodiments, arrays of multi-electrode micropores and their characterization are described. Experimental results at micropores have shown that small volume analysis is possible and that advantages of micropores over the other structures include multiple drop analysis. A flexible substrate makes the micropore useful in locations that are not suitable for rigid electrochemical devices and the pores may be advantageously deployed in flow-through detector applications. The addition of a third electrode layer and formation of a reference electrode can further improve performance in small volume analysis. In both the microcavity and micropore systems, the addition of subsequent layers of insulator and conductor can increase the numbers of electrodes used in small volume experiments as well as the functionality of the device. One of the significant advantages of this invention is that these microcavities and micropores are readily adapted to existing monitoring, detecting and experimental techniques.

Flux of solution species to small electrodes is dominated by radial diffusion, resulting in a high flux per unit area. Consequently, microelectrodes can be fouled readily. The electrodes can be cleaned by electrochemically cycling the potential several times. This is a common method to clean electrodes without requiring direct contact with substances like polishing cloths and polishing compounds.

Electrodes within the cavities are located very close to each other. Thus, electrochemical products generated at one electrode may be collected or interfere with the electrochemistry of another. This creates both difficulties and advantages. Readings by a reference electrode may be altered by molecules interacting with a nearby working electrode. The time scales of the experiments can be controlled to avoid this problem. Also, care can be taken so that electrogenerated products are irreversible and no longer electroactive and capable of interfering with adjacent electrodes.

The close proximity of electrodes within these microstructures can be used to amplify detection of various molecules. The microstructure may contain a detection chemical capable of performing a reversible electrochemical reaction with the compound being detected. By utilizing a reversible reaction, the detection chemical may travel back and forth between electrodes many times so long as the compound being detected is present. This results in amplification of the electrical signal created by the presence of the compound being detected. This allows detection of extremely small concentrations of chemicals.

Novel and unusual features:

(a) The electrodes are small in size. Consequently, the flux per unit area is much larger than at macroscopic sized electrodes, thereby providing a larger current (or signal) per unit area. Radial diffusion is also dominant at micro and nanoelectrodes, yielding steady state currents, which facilitates measurement of the current over the time-dependent current of macroelectrodes. The small size of the microcavities also makes it possible to make measurements in solutions having high resistance.

(b) This design is unique because it contains the entire electrochemical cell in one small volume. One electrode could easily be coated with Ag to create an Ag/AgCl reference. The electrodes should be isolated from the convective flow because they are located in a cavity.

One of the main advantages of microelectrodes located in a microcavity is their ability to isolate the working electrode from convective fluxes in the bulk solution. They reduce noise in amperometric detection by eliminating small current variations from random convection fluctuations. In all of the examples present in the known art, only the working electrode is located in the cavity. The design presented here can contain two electrodes that serve as reference and working electrodes.

(c) Thin films may be suspended across the cavity. The material may be a polymer or biological in nature, such as a bi-layer lipid membrane (BLM), which is made up of two monolayers of amphiphilic molecules in a tail-to-tail configuration. The film serves as a filter to substances from without and within the cavity.

Polymers and BLMs have been used for electrochemical sensors for many years. The BLMs have been used previously by others in similar applications but the known design consists of only a single Ag/AgCl reference electrode fabricated onto a glass microscope slide and then fused to etched silicon. This limits the analytical applications to systems that exhibit a change in the conductance through the membrane. The present invention is not limited in such a manner but will facilitate this type of analysis, as well as direct redox chemistry inside the cavity.

(d) Surface of material around the cavity is controllable in chemistry, wetting, orientation, and composition. Such flexibility in the chemistry around the openings will allow optimization of adhesion or association of suspended films surrounding the cavity.

(e) The surfaces of any parts of the device are modifiable to increase or decrease the wetting properties. This is important so that different solvents and solutions can be used and that will fill the cavity. For example, conductors, such as metals, can be modified with organothiols and insulator materials, such as $SiO_2$, or $Si_3N_4$, can be modified with organohalogensilanes or organotrialkoxysilanes. Hydrophilic compounds will allow polar solvents and solutions to wet the cavities. Hydrophobic compounds will allow non-polar solvents and solutions to wet the cavities.

(f) Electrodes can be placed within nanometers of the location of the suspended film. This makes it easy to measure diffusion through the film because of small time scales. This is a phenomenon that plagues ion selective electrodes in which electrodes are typically several microns or more away from the film. The closer the electrodes to the film the faster the response time (analysis time for a given chemical).

Other techniques that use phospholipid bilayers as the film include patch clamp devices and bilayers across pinholes in Teflon sheets. In both cases, electrodes on either side of the bi-layer are macroscopic in size an cannot be positioned close enough to the bilayers to monitor diffusion. In fact, these techniques only monitor capacitance of the bilayers or changes in conductivity of ions through them, where electrodes do not need to be located adjacent to the bilayers. Bilayers across the electrode-containing cavities of the present invention will allow not only capacitance and conductivity measurements to be made, but also monitoring of diffusion of species, such as redox couples that can be generated on one side and detected on the other.

There are existing techniques that use microelectrodes and microelectrode arrays that are coated with films of materials that are of interest in chemical sensing. In these cases, the electrodes are placed immediately adjacent to the film. However, because the solid substrate with electrodes is on one side of the film, diffusion of species completely through it is blocked. There is also the problem of the effect of the substrate on the properties of the film and the permeability of the film. The technique of the present invention eliminates that problem and allows the electrodes to remain within close proximity to maintain fast time scales in detecting diffusing species.

(g) The cavities are constructed into a single substrate or within layers of materials that are sandwiched together prior to cavity formation. This eliminates changes in the dimensions of the hole or composition of the materials or surface around the cavity that might occur if materials were bound or fused post-cavity formation.

(h) One or more electrodes can be constructed inside the cavity. The number is only limited by the wall height, and the insulator and conductor layer thicknesses. Known art used only one electrode inside the cavity and did not allow for easy construction of multiple electrodes in the same cavity.

(i) The cavities hold very small volumes of samples for analysis. These cavities can also contain enough electrodes to provide a self-contained electrochemistry of the sample. Several other researchers have attempted to miniaturize electrochemical cells. The volume of their cells are typically in the μL range. The design presented here gives volumes that are nominally in the pL or as low as the fL range. With proper design of the substrate, the volume of sample required for the analysis would be minimized. This is important because of the necessity to minimize the sample volumes when dealing with toxic waste or precious body fluids or expensive reagents or substances like DNA.

(j) Cavity widths can be varied depending on the design of the microfabrication mask.

(k) Cavity depths can be varied. This can be done by changing the number and thickness of the layers of materials and the depth to which these materials are etched in forming the cavity.

(l) Any number of cavities can be constructed onto a substrate, from one to hundred or thousands per unit area. The limitation in number is based on the size of the cavities themselves and allowing enough material between them to provide sturdy walls. This is advantageous for providing multifunctional properties in small areas of a substrate (each cavity has a different function or senses a different chemical). In addition, the sizes of the cavities can be made very small, much smaller than traditional methods for making ion selective electrodes, for example.

(m) The substrates of the present invention here and the deposition processes for formation of insulator and conductor layers as well as the microfabrication schemes of the present invention are all well suited to easy scale-up to mass production.

Uses for the invention.

(a) Self-contained electrochemical cells that have from one to many micro or nano-sized electrodes and only require femtoliter (fl) to picoliter (pL) volumes to be measured. A cavity of 1 micron radius and 1 micron depth has a volume of:

$$V = \pi r^2 h = \pi \times (1 \times 10^{-4} \text{ cm})^2 \times 1 \times 10^{-4} \text{ cm} = 3 \times 10^{-12} \text{ mL} = 3 \text{pL}$$

Such small volumes are important for valuable samples such as those containing proteins or DNA. Even if analysis does not have to be restricted to small volumes, the electrodes are so small that they will not perturb the chemical composition significantly.

(b) Electrochemical detectors in flowing streams (e.g., as detectors in separations methods like high performance chromatography, as monitors of electroplating baths, as detectors in microfluidic systems, etc.). The electrochemical cells are self-contained and do not require a reference or counter electrode downstream from the working electrode. Analysis can also be done in flows of small volumes of materials and allow a stable signal that is not influenced by the "noise" of variations in flux. The cavity helps to dampen the convection before analyte arrives at the electrodes within it. The dampening of convection for recessed electrodes has been reported. However, that for a complete electrochemical cell has not been carried out.

(c) Chemical sensing. Thin films suspended across the cavities can filter out unwanted analytes and filter in wanted ones without touching the electrode surface. Therefore, there is no restriction of the analyte in passing completely through the film (not blocked on one side). This is especially useful for measuring conductance of ions through the films.

One possible chemical sensor is the development of ion sensors. Microfabricated structures bridged by suspended membranes, with electrodes constructed outside and inside the cavities, can function as ion-sensing devices. The ion channel, gramicidin A, is an excellent candidate because of the extensive literature on its structure and behavior. The phospholipids that form the suspended bi-layer membrane may contain phosphatidylcholine, a neutral moiety, or phosphatidylserine, which is negatively charged at neutral pH. Leakage of suspended membranes without ion channels and selectivity of those with ion channels may be measured using electroactive probe molecules (e.g., $Fe(CN)_6^{3-/4-}$, $Ru(NH_3)_6^{2+/3+}$, $Ag^+$, $I^-$, $Ph^{2+}$). The quantitative capabilities of the ion-sensing devices may be evaluated by recording the amperometric response of electrodes inside the cavity to various concentrations of analyte outside of the membrane. Selectivity and quantitative determination of non-electroactive ions (e.g., $Li^+$, $Na^+$, $K^+$, $NH_4^+$, $Ca^{2+}$, $NO_3^-$, $Cl^-$) with various counterions can be evaluated by conductivity measurements through suspended membranes. Voltage gating by a different kind of ion channel, such as alamethicin, provides a means to block the passage of ions or to switch an ion sensor on and off.

(d) Biomimetic applications.

Assembly of phospholipid bilayers and fusion of phospholipid vesicles with bilayers suspended across microfabricated cavities can be evaluated as a function of time, concentration, and composition. These processes are important in understanding transport of newly synthesized membrane constituents, the pathway of conduction of nerve impulses, and infection of cells by viruses. Fusion has been studied using fluorescing molecules and model vesicles. One can use fluorescence to monitor mixing of the molecules into the membranes (via fluorescent-tagged lipids) and leakage out of vesicles (via fluorescein) during fusion. The microstructures of the present invention will allow such processes to be followed not only by fluorescence, but also in other ways that have not previously been possible or convenient, such as by electrochemistry.

For example, a device in accordance with the present invention may generate species electrochemically near the outer face of the bilayer and allow collection of these species inside the well at the inner face of the bilayer. The electrodes located just outside the bilayer may be either positioned by a micromanipulator or patterned directly onto the substrate with microfabrication. This technique will allow study of the process of membrane assembly in real time. A steady state faradaic current can be set up between generator and collector prior to the introduction of vesicles. As assembly across the gap commences, the diffusion of electroactive species, and thus, the steady state current, will be perturbed, and eventually stopped when an impenetrable membrane is formed. If a preexisting bilayer is present and fusion to vesicles is being studied, the species electrogenerated on either one or both sides of the membrane can be detected on the other side to follow leakage. Simultaneous monitoring of the assembly with spectroscopic techniques, such as fluorescence, provides complementary evidence of membrane formation.

Local variations in pH at either the inner or outer sides of the membrane are also conveniently produced with the microstructures, because $H^+$ and $OH^-$ can be generated by oxidation or reduction of water, respectively, at electrodes near the membranes. For example fusion of membranes made of N-methyldioleoyl-phosphatidyl-ethanolamine, is pH dependent, and can be used.

(e) Drug delivery devices.

The devices should also be useful in controlling the dispensing of the contents of the cavities. This is similar to a microencapsulation technique. Microencapsulation methods are of interest in pharmaceutical, agricultural, adhesive, flavor and fragrance, and ink technologies. The current closest known application to the present invention is microencapsulation of chemicals in liposomes. A problem with most encapsulants is the limited control available for dispensing the contents. Often the coating of the capsule regulates the extent of dispensing of the internal components. For in vivo applications, liposomes can be removed before they are activated or are concentrated in unwanted tissues. The suspended membranes across the cavities in accordance with the present invention will allow control of dispensing via application of an electric field between electrodes on either side of the membrane. However varied extents of porosity due to electroporation and the presence of voltage-gating biological molecules will provide a means of controlled delivery of chemical species as a function of potential, without destroying the membranes. Membrane structures can include those made from DMPC (dimyristoyl phophatidylcholine) or DPPC (dipalmitoyl phosphatidylcholine).

Target species can include electroactive molecules as well as molecules of practical interest, including insulin and estradiol. Insulin has importance in regulating diabetes. Electronic dispensing of insulin that is automated, based upon measurements of glucose level can provide a desirable solution to controlling diabetes. In addition, reports claim that small amounts of phospholipid will not be harmful, and thus, such materials are good candidates as biocompatible encapsulating materials. Estradiol is a steroid important to promoting and maintaining sex characteristics and in sexual development of women. Derivatives of estradiol are important in contraceptives for women, and require regulated release. Variation in membrane integrity can be studied in the presence of various concentrations of estradiol. Estradiol has a structure similar to cholesterol and will likely partition into the bi-layers and change membrane stability and mobility.

(f) Chemical assays.

Chemical assays can be constructed using multiple cavities on a single substrate. These do not necessarily have to be electrochemical in nature and can test for multiple substances on a small area. Different films or materials may be suspended or patterned into each well. Each material may be sensitive to a different analyte or provide different chemical filtering capabilities or fluorescing capabilities.

One object of the invention is to provide a microstructure device which is a self-contained electrochemical cell.

Another object of the invention is to provide a microstructure device with integrated, independently-addressable electrodes.

Another object of the invention is to provide a microstructure device with a membrane which selectively permits mass transfer of analytes across the membrane, depending on the chemical composition of the analytes.

Another object of the invention is to provide a microstructure device for acting as a chemical sensor.

Another object of the invention is to provide a microcavity device for rapid detection and analysis of an analyte in the microcavity.

Another object of the invention is to provide a microcavity device which has both band electrodes and disk electrodes.

Another object of the invention is to provide a microstructure device which has tubular nanoband electrodes.

Another object of the invention is to provide recessed microdisk electrodes.

Another object of the invention is to provide a microstructure device with at least two electrodes.

Another object of the invention is to provide a microcavity device where a diameter and a depth of the microstructure is less than one millimeter.

Another object of the invention is to provide a microcavity device where the volume of the microstructure is between on femtoliter an one milliliter.

Another object of the invention is to provide a method for producing predominantly diffusion mass transfer of an analyte into a microcavity chemical sensor.

Another object of the invention is to provide a method for microfabricating recessed disk microelectrodes.

Another object of the invention is to provide a recessed disk microelectrodes with gold conducting layers separated by polyimide insulating layers.

Another object of the invention is to provide a method for fabricating microcavity devices with recessed disk microelectrodes and tubular nanoband electrodes.

Another object of the invention is to provide microstructure devices with gold and copper conducting layers separated by insulating layers.

Still another object of the invention is to provide a microstructure device which can detect the presence of amino acids.

Yet another object of the invention is to provide a method for detecting amino acids in microstructure devices.

DETAILED DESCRIPTION OF THE PREFERRED EMBODIMENTS

Exemplary embodiments of the present invention include constructed devices that contain cavities or similar structures including pores, holes and the like that are generally microscopic (<1 mm) in width and depth and contain any number of individually-addressable electrodes, separated by insulators, along the walls of each structure and/or at the bottom of the cavity. The conducting and insulating materials are deposited alternately onto the starting substrate, which is typically an oxidized silicon wafer but may be any substrate susceptible to methods of electrode deposition, such as thermal evaporation, electron beam evaporation, sputtering deposition, spin coating, molecular beam epitaxy or the like. The cavities are etched through these layers, perpendicular to the plane of the substrate, exposing the layers at their edges. The bottom of a cavity may also consist of an electrode or have a microfabricated-patterned electrode. Alternatively, pores may be carved entirely through the device. Any of the electrodes in the cavities and pores may be modified and used as reference electrodes or working electrodes, allowing complete electrochemical experiments to be performed within the structures. The structures also offer some protection from convection currents in surrounding solution. The cavity may hold as little as a few femtoliters in volume. The top surface, surrounding the cavities may be modified to enhance or diminish assembly of thin film materials across the cavities. These thin film materials may be polymers or assemblies of molecules such as phospholipid bilayers or bilayer lipid membranes (BLMs) that eliminate or control access of other species into and out of the cavity.

Photolithography and thermal evaporation are combined and used to deposit alternating insulating and conducting layers onto a substrate to form microcavities. Both of these methods are well known to those skilled in the art of microfabrication. It is also known to those skilled in the art that other methods will work equally well to form microcavities and micropores. Two procedures, lift-off processing and etching may be used to form microelectrodes in microcavities.

Figure 1:
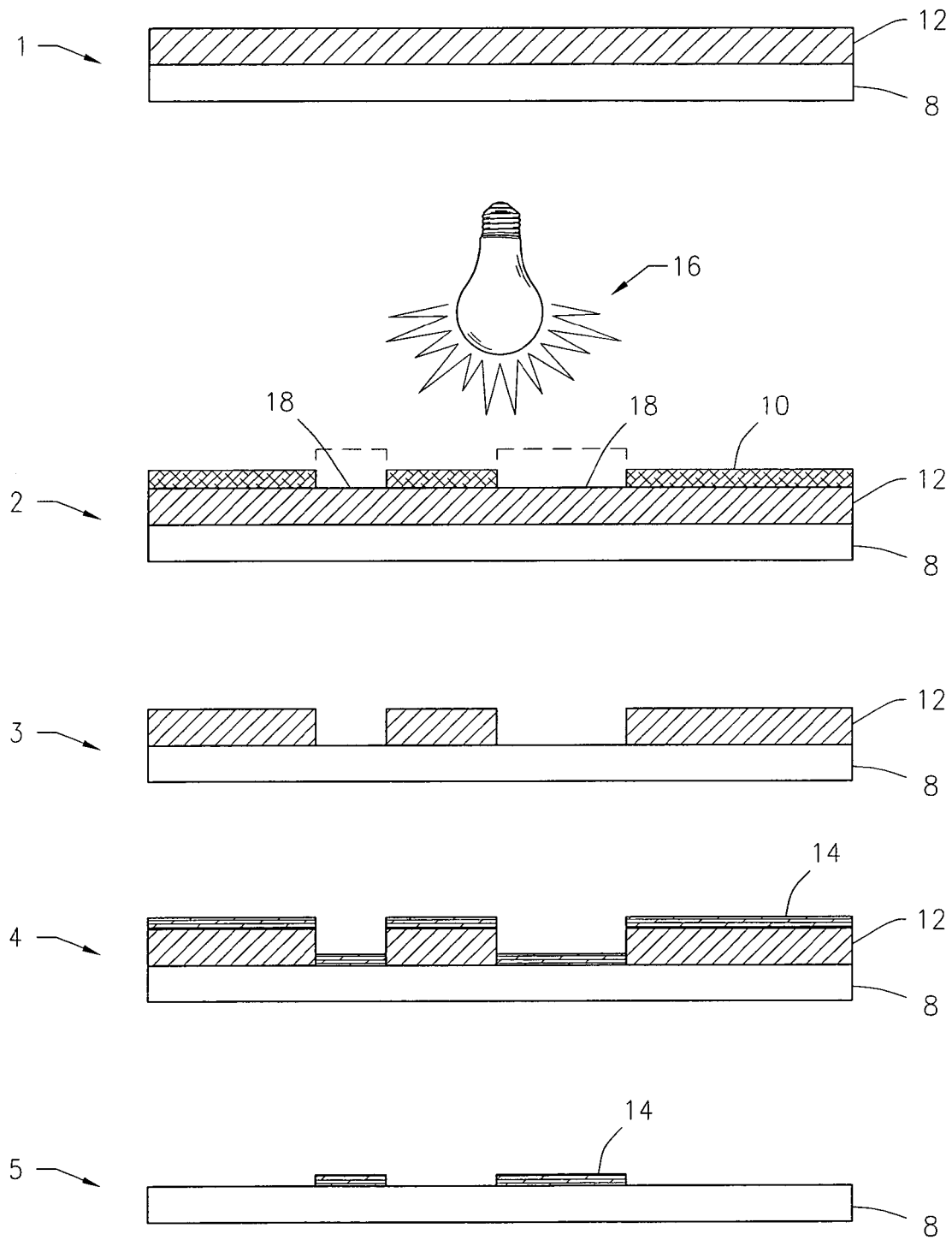
FIG. 1 is a schematic diagram showing a general microfabrication process known as lift-off processing used to construct a patterned layer of a microcavity device.

The lift-off processing method is shown in FIG. 1. To add a layer 14, which may be either a conducting or an insulating layer, to the substrate 8, photoresist 12 is applied in the first step 1. In the second step 2, mask 10 is laid over photoresist 12 and Ultraviolet (UV) light 16 develops the exposed portions of the photoresist 18. The mask 10 is then removed during the third step 3 and the new layer 14 is deposited by thermal evaporation (or other methods listed above) in the fourth step 4. Finally, in the last step 5, the remaining undeveloped photoresist 12 is removed, taking with it portions of layer 14 covering the photoresist 12. This leaves a layer 14 that has been formed into a pattern that is inverse to the pattern on the mask 10.

Figure 2:
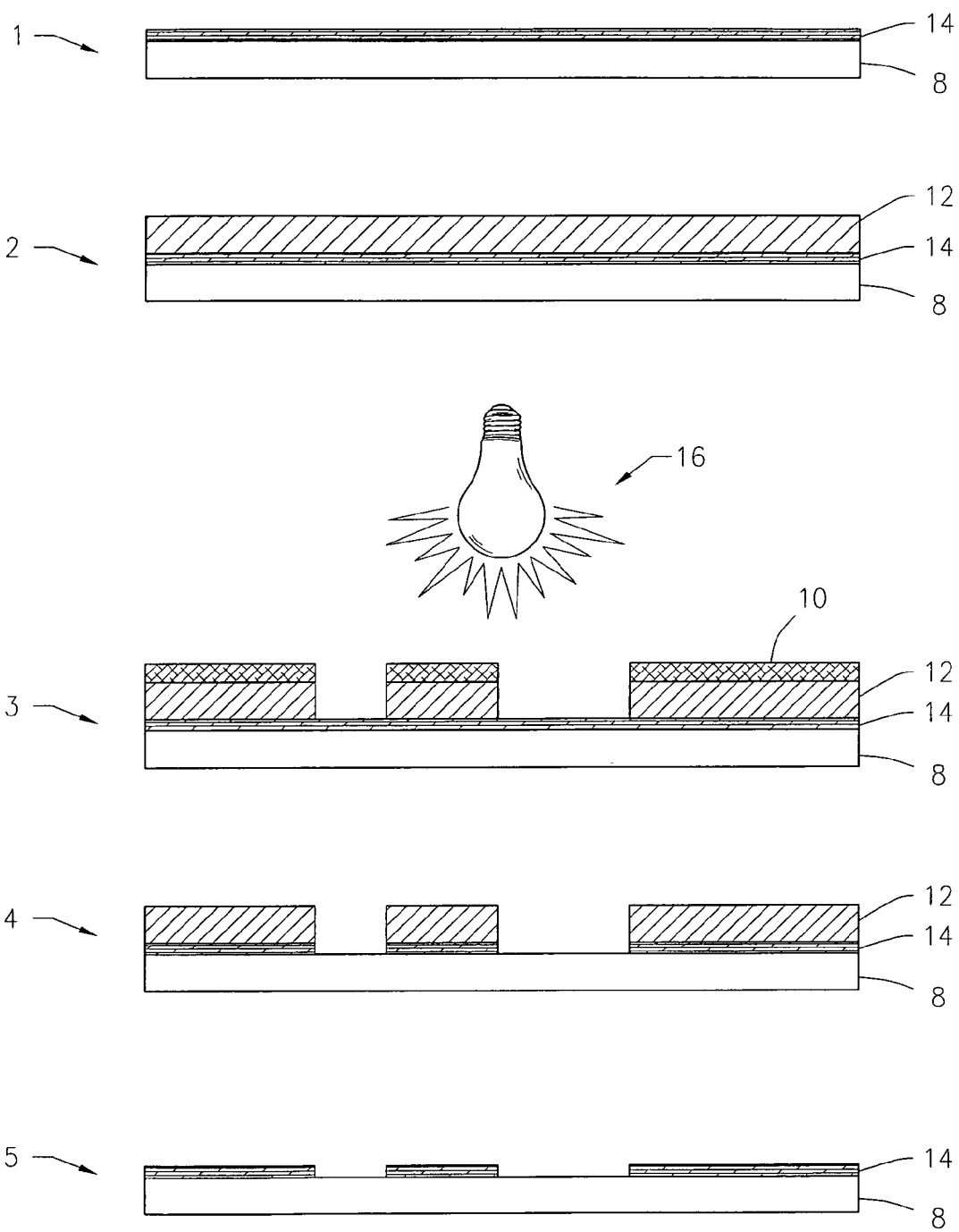
FIG. 2 is a schematic diagram showing an alternative general microfabrication process known as etching used to construct a patterned layer of a microcavity device.

The etching microfabrication technique is shown in FIG. 2. During the first step 1 the new layer 14 is thermally deposited on substrate 8. In the second step 2, photoresist is coated onto the new layer 14. During the third step 3 a mask 10 is placed over the photoresist, UV light 16 develops exposed portions of photoresist 12, and those portions are washed away, leaving some portions of layer 14 exposed. In the fourth step 4, mask 10 is removed and exposed portions of layer 14 are etched away (thus the name of this method). Finally in step 5, the remaining photoresist 12 is washed away, leaving a layer 14 that is formed into a pattern the same as that of mask 10.

Figure 3:
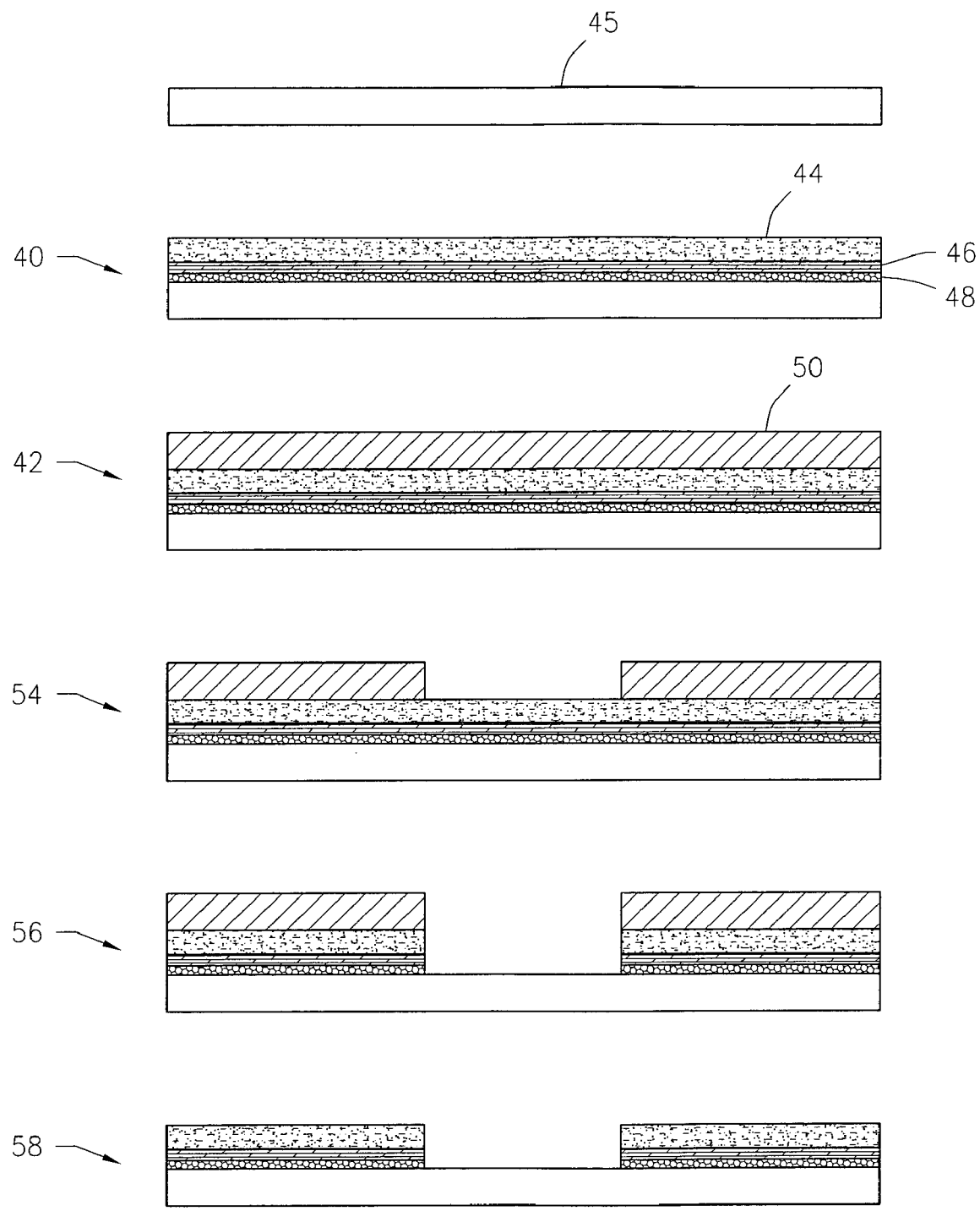
FIG. 3 is a schematic diagram showing a general microfabrication process to construct a device having two layers.

Etching may be used to form a single band electrode in one easy cycle of photolithography, as shown in FIG. 3. In step 40, a glass substrate is coated by thermal evaporation with successive layers of chromium 48, gold 46 and sodium nitride, an insulator, 44. Photoresist 50 is then applied in step 42. In step 54 UV light is applied through a mask and developed photoresist 50 is washed away, leaving exposed thermally deposited layers. In step 56 layers 44, 46 and 48 are etched away. Finally in step 58 photoresist 50 is completely removed. This results in a recessed tubular band microelectrode.

Figure 4:
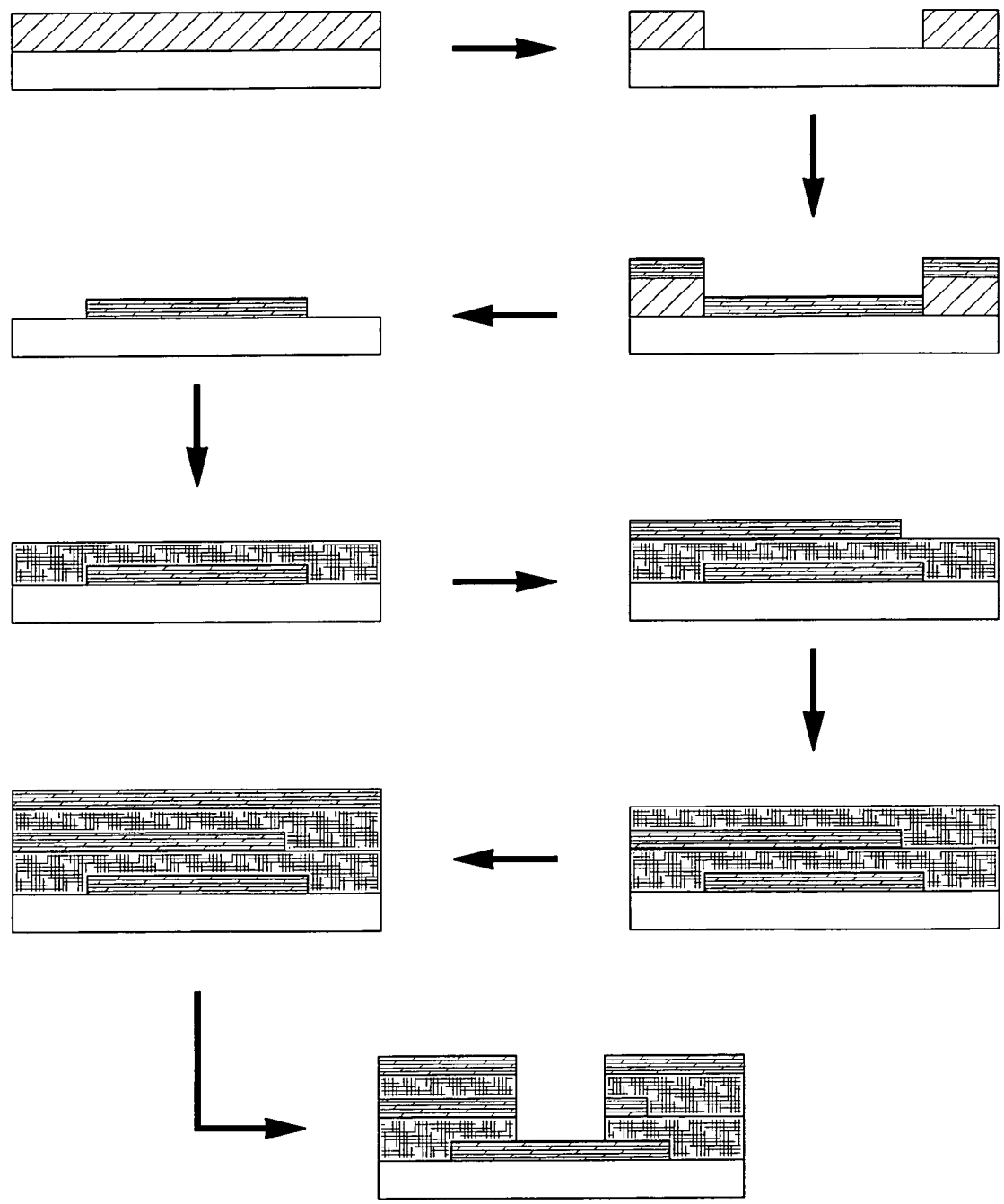
FIG. 4 is a schematic diagram showing a general microfabrication process used to construct a microcavity device having a RMD, a tubular nanoband electrode and a top reference electrode.
Figure 18:
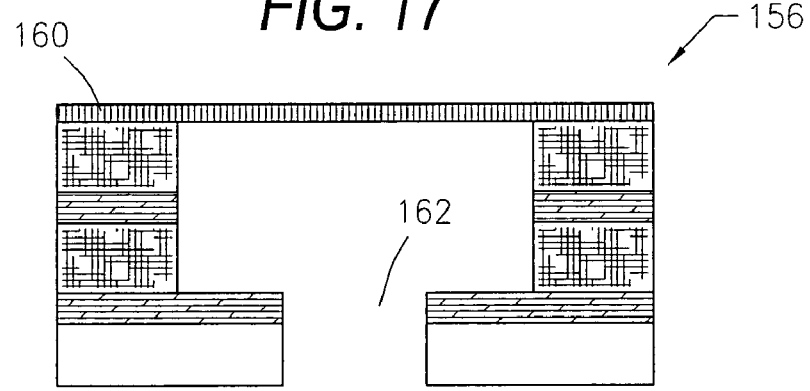
FIG. 18 is a schematic view that shows a structure for three-dimensional microfabricated devices having a lipid membrane spanning the opening to the microstructure and a hole in the bottom.
Figure 19:
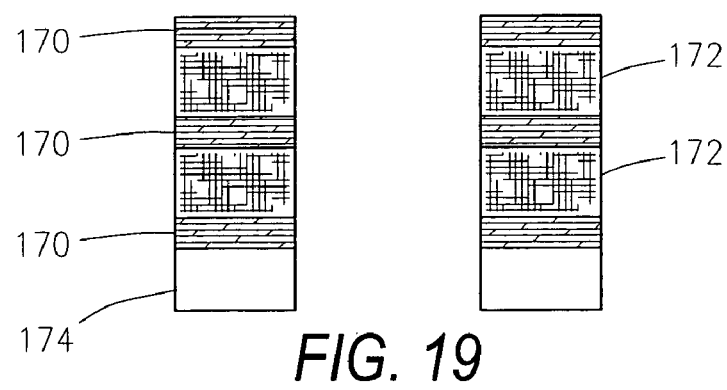
FIG. 19 is a schematic diagram that shows a micropore fabricated by layering alternating conductor (e.g., gold, platinum, carbon, etc.) and insulator materials (e.g., polyimide, $SiO_2$, silicon nitride, etc.) with edges of these layers are exposed along the walls of the micropore to show dimensions of cavity diameter and depth.

These methods may be used to form a variety of microfabricated electrochemical cells. Cavities may be as little as 5 micrometers in diameter and fewer than 4 micrometers deep. FIG. 4 shows a process for forming a completed microcavity. The procedures described above are used in succession in order to form a microcavity having an RMD electrode and two TNB electrodes. These processes work equally well on rigid and flexible substrates and may also be used to form micropores as shown in FIGS. 18 and 19.

Figure 5:
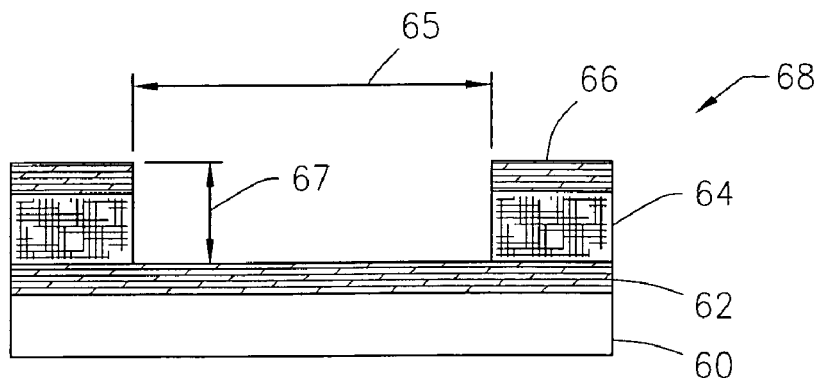
FIG. 5 is an enlarged schematic diagram showing a three layer microcavity fabricated by alternating layers of conductor (e.g., gold, platinum, carbon, etc.) and insulator materials (e.g., polyimide, $SiO_2$, silicon nitride, etc.) with edges of these layers exposed along the walls of the cavity, cavity diameter and depth are shown.

FIG. 5 shows a single recessed microdisk (RMD) electrode cavity 68 comprising a substrate 60, a RMD electrode 62, and insulating layer 64 and a top layer 66 that is applied to make the structure more rigid, better defined and reproducible. RMD cavity 68 has a diameter 65 that can be as little as 10 μm and a height 67 that ranges from about 4 micrometers to several hundred micrometers.

Figure 6:
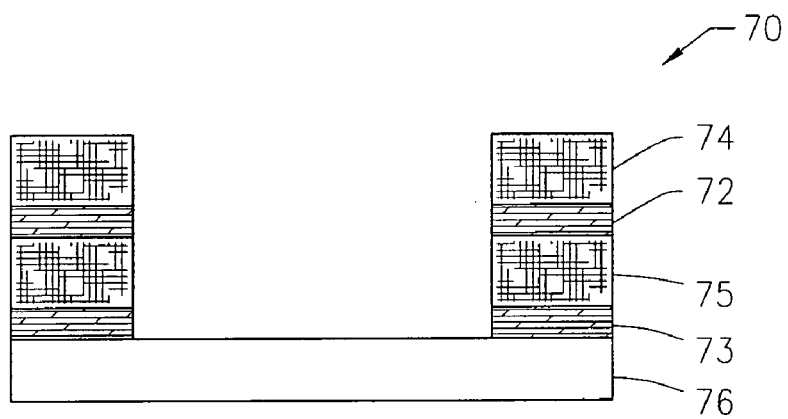
FIG. 6 is an enlarged schematic diagram of a cross section of a microcavity fabricated by alternating layers of conductor (e.g., gold, platinum, carbon, etc.) and insulator materials (e.g., polyimide, $SiO_2$, silicon nitride, etc.) with the edges of these layers exposed along the walls of the cavity, forming two tubular nanoband microelectrodes in the microactivity.
Figure 7:
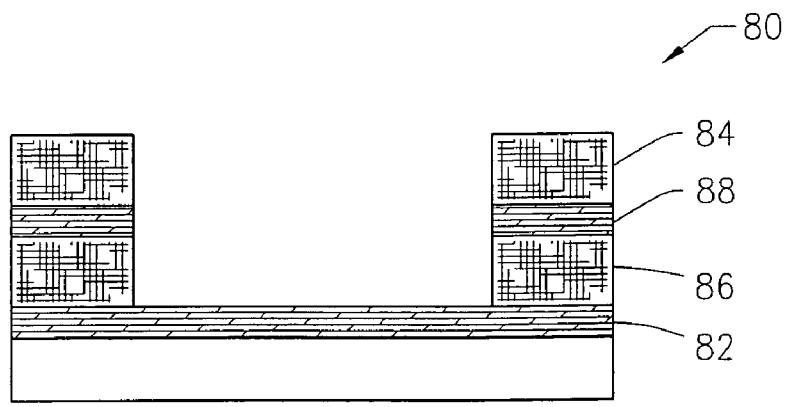
FIG. 7 is an enlarged schematic diagram of a cross section of an alternative microcavity fabricated by alternating conductor (e.g., gold, platinum, carbon, etc.) and insulator materials (e.g., polyimide, $SiO_2$, silicon nitride, etc.) with the edges of these layers exposed along the walls of the cavity forming one tubular nanoband microelctrode and one recessed disk microelectrode in the microactivity.

FIG. 6 shows another alternative design. Microcavity 70 contains two tubular nanoband microelectrodes 72 and 73 and two insulating layers 74 and 75 attached to substrate 76. Microcavity 70 also has a diameter that may be as little as 10 micrometers or greater than 100 micrometers. It is generally desirable for microcavity 70 to have a small diameter to increase the speed of electrochemical detection. FIG. 7 shows microcavity 80 having two insulating layers 84 and 86, a recessed disk microelectrode 82 and a tubular nanoband microelectrode 88.

Figure 8:
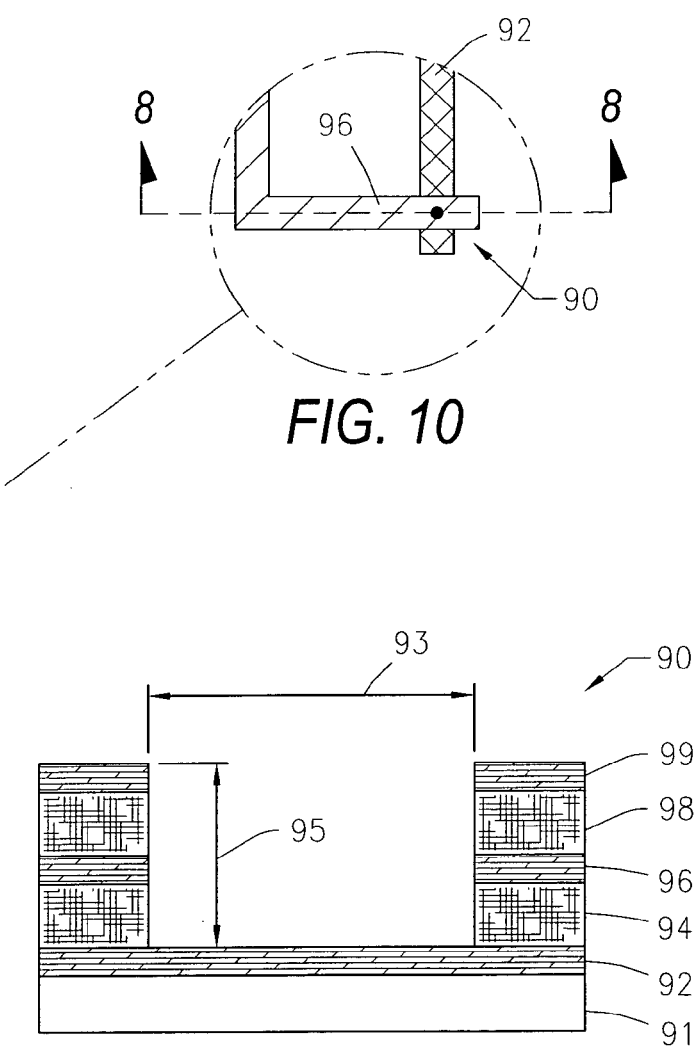
FIG. 8 is an enlarged schematic cross section of a five layer microcavity having a RMD and two nanoband microelectrodes.

FIG. 8 illustrates yet another variation of the disclosed invention. Microcavity 90 extends four layers above a RMD.

Figure 9:
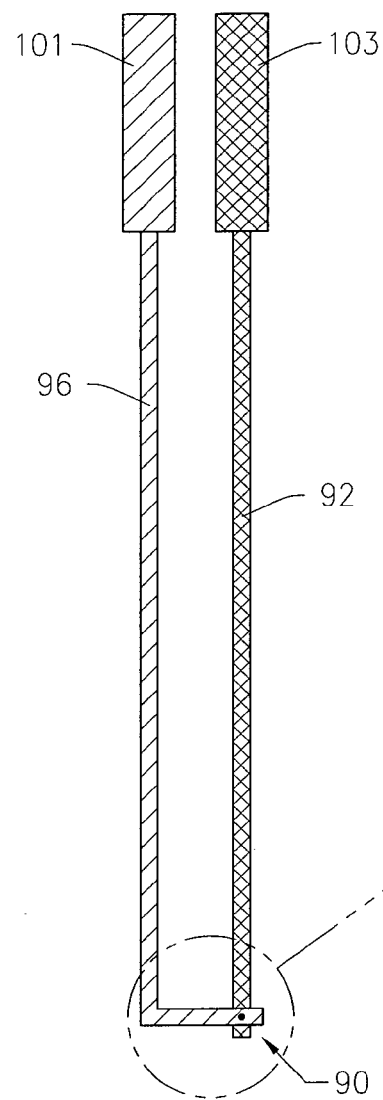
FIG. 9 is a top plan view of one design of a microcavity, showing how connections can be made to each layer of conductor, so that each edge electrode may be independently addressable.
Figure 10:
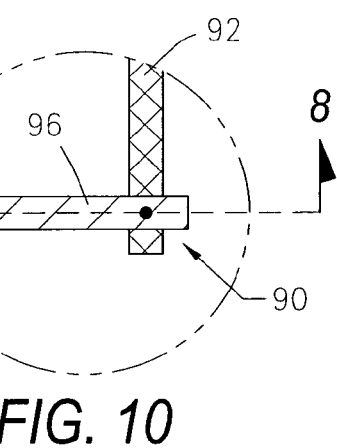
FIG. 10 is an enlarged top plan view of a portion of FIG. 8, showing how connections can be made to each layer of conductor, so that each edge electrode may be independently addressable.

On top of substrate 91 lies RMD layer 92. Insulator layer 94 separates RMD 92 from TNB electrode 96. Insulating layer 98 separates TNB electrode 96 from a top conducting layer 99. Top layer 99 is deposited in order to add definition and strength to the structure. Diameter 93 may be as little as 10 micrometeres, and height 95 may be as little as 4 micrometers. FIG. 9 shows the same microcavity from the top, illustrating how microelectrodes 92 and 96 in a microcavity 90 may have macroscopic leads 101 and 103 according to the present invention. FIG. 10 is an enlarged view of microcavity 90 from FIG. 8 to better illustrate the geometry that allows this unique feature.

Figure 11:
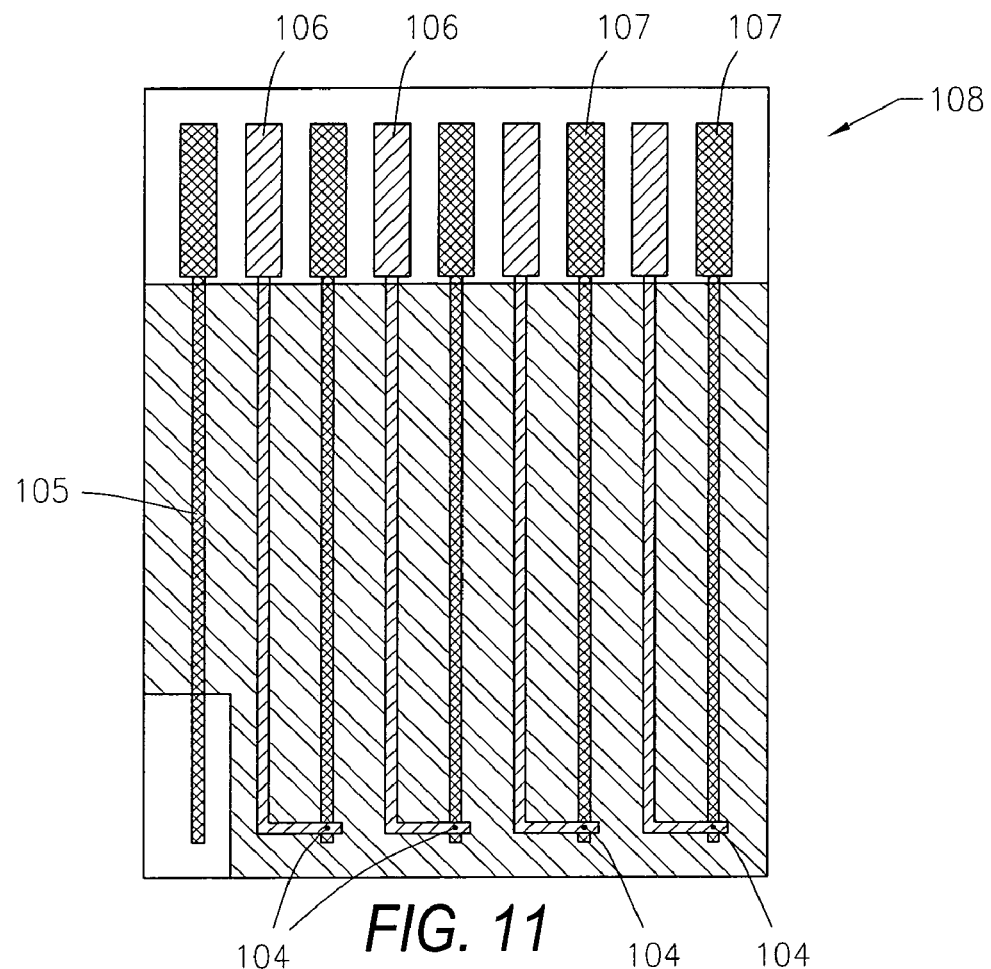
FIG. 11 is a top plan view of one design of an array of microcavities, showing how each microcavity may have two independently addressable microelectrodes and a third electrode common to all cavities of the array.

FIG. 11 shows a series of microcavities 104 with macroscopic electrode leads on an array 108. A larger number of microcavities may be arranged on a single small substrate. Electrodes 107 form the first electrodes within the microcavities and may be either RMD's or TNB's. Electrodes 106 form TNB's in their respective microcavities. Top layer 105 may be used as a reference electrode, or used simpley to provide stability to the structure.

Figure 12:
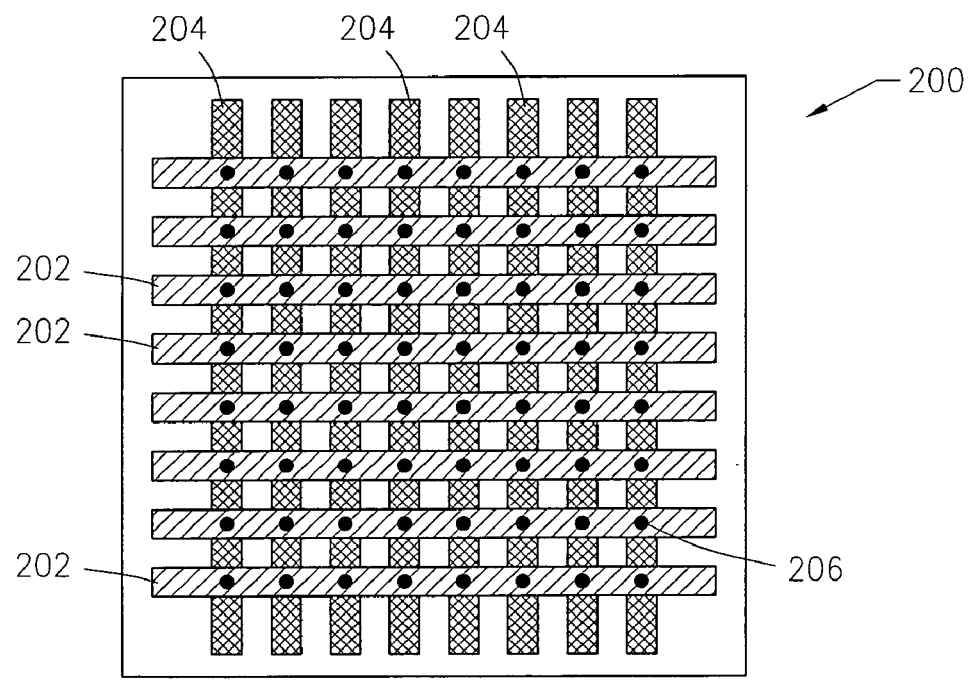
FIG. 12 is a top plan view of an alternative design for an array of microelectrodes.

FIG. 12 shows an alternative microcavity array 200. Eight top electrodes 202 are parallel to one another and perpendicular to the eight bottom electrodes 204. This allows the formation of 64 cavities 206 over a very small area.

Figure 13:
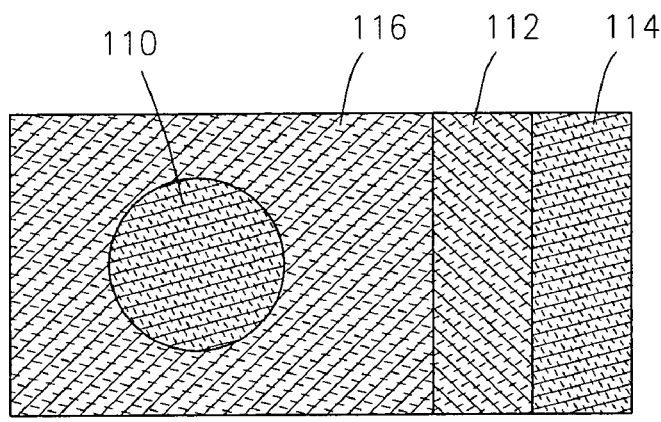
FIG. 13 is a top plan view of another design for a microfabricated cavities having independently addressable microelectrodes.
Figure 14:
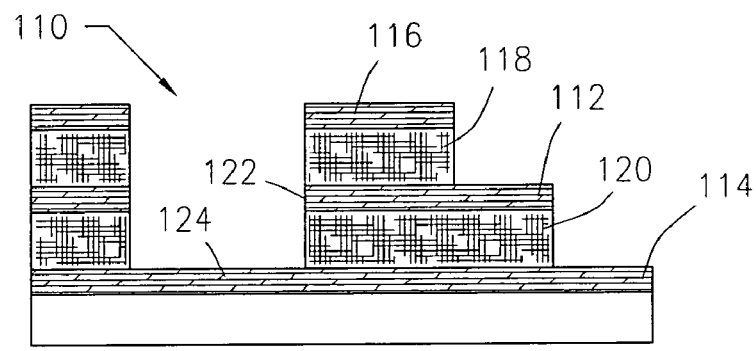
FIG. 14 is a cross-sectional view taken along line 113 in FIG. 13 showing the independently addressable microelectrodes.

FIGS. 13 and 14 show an alternative geometry to that shown in FIGS. 8, 9 and 10. Microcavity 110 contains a TNB electrode 122 and a RMD electrode 124. These have corresponding contact pads 112 and 114 respectively and are separated by insulating layer 120. Insulating layer 118 and top conductor layer 116 complete the microcavity. Layer 116 is not necessarily used as an electrode, but is applied to add rigidity to the microcavity. This version of the invention has a simpler geometry and allows contact pads 112 and 114 to be very large.

Figure 15:
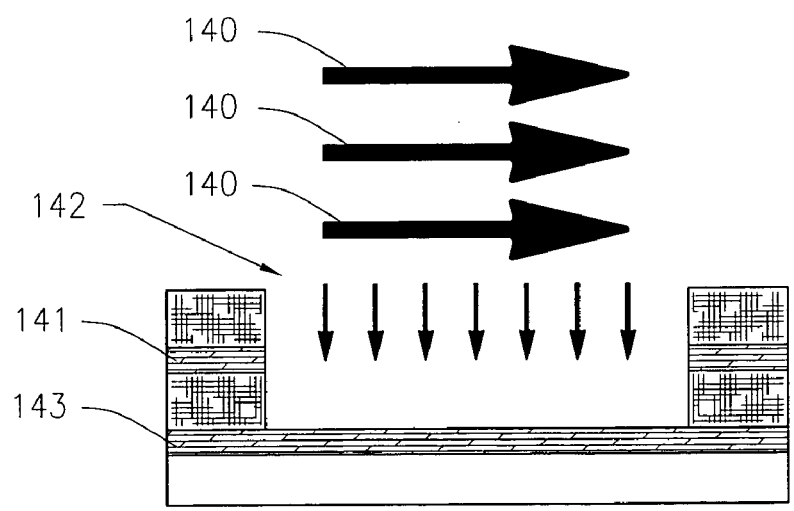
FIG. 15 is a schematic diagram that shows how recessed electrodes can be isolated from convective flow (stirring, flowing stream, etc.) to reduce noise in the electrochemical response because the flux of species to the electrodes would not be perturbed by the convection.
Figure 16:
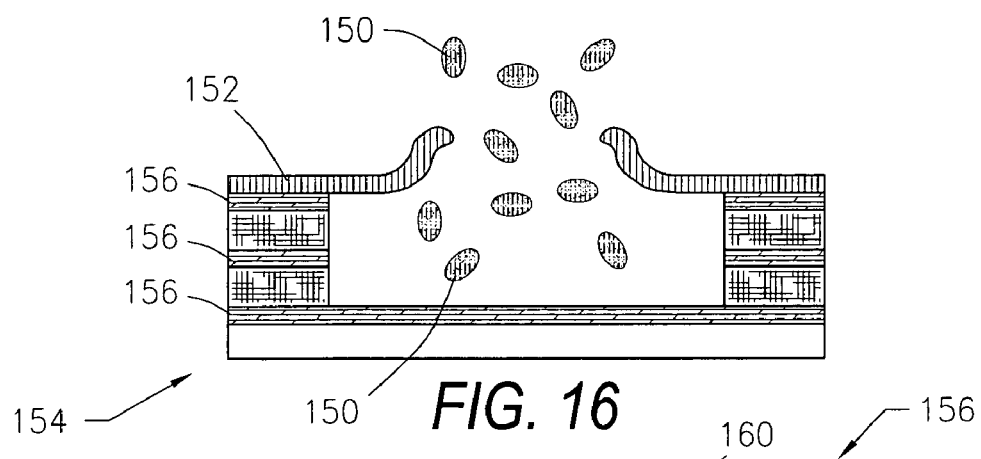
FIG. 16 is a schematic diagram of a chemical delivery device and process. Substances encapsulated within the cavity and covered with a suspended film can be released into the surrounding environment in a number of different ways. One is a change in osmotic pressure, a second is an applied potential across the film, and a third is association of molecules with the membrane from solution that disrupt the integrity of the film.
Figure 17:
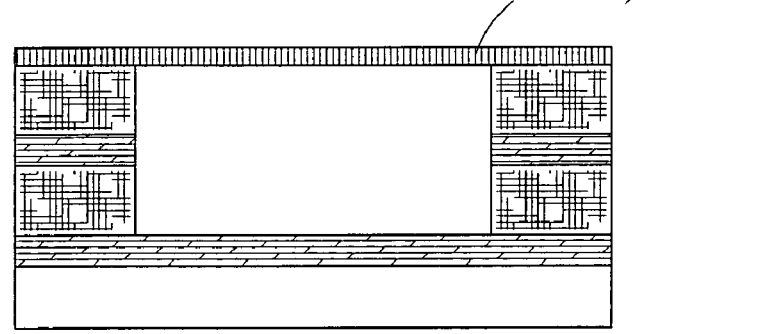
FIG. 17 is a schematic diagram that shows a structure for microfabricated devices having a lipid membrane spanning the opening to the microcavity.

FIGS. 15, 16, 17 and 18 illustrate various uses for the invention. FIG. 15 illustrates how TNB electrode 141 and RMD 143 in microcavity 142 are protected from convection currents 140 in solution. This increases their accuracy. FIG. 16 shows a microcavity 154 having a lipid bi-layer covering it. When a current is applied to one of the conducting layers 156, electroporation results releasing particles 150 that were trapped in the microcavity. This may be used to release drugs or other chemicals into an environment. It allows release of the particles at a specific time in a specific amount. FIGS. 17 and 18 show microstructures 156 also covered by lipid bilayers 160. These may be used to study diffusion or transport across a lipid membrane. The lipid bilayer may also be used as a filter, adding selectivity to the microcavity. In FIG. 17 a pore 162 is drilled into the bottom of the cavity so that osmotic pressure does not rupture the lipid bi-layer. FIG. 19 shows a micropore 168 having a substrate 174 conducting layers 170 and insulating layers 172. Micropores have a variety of uses as described in this specification.

Figure 20:
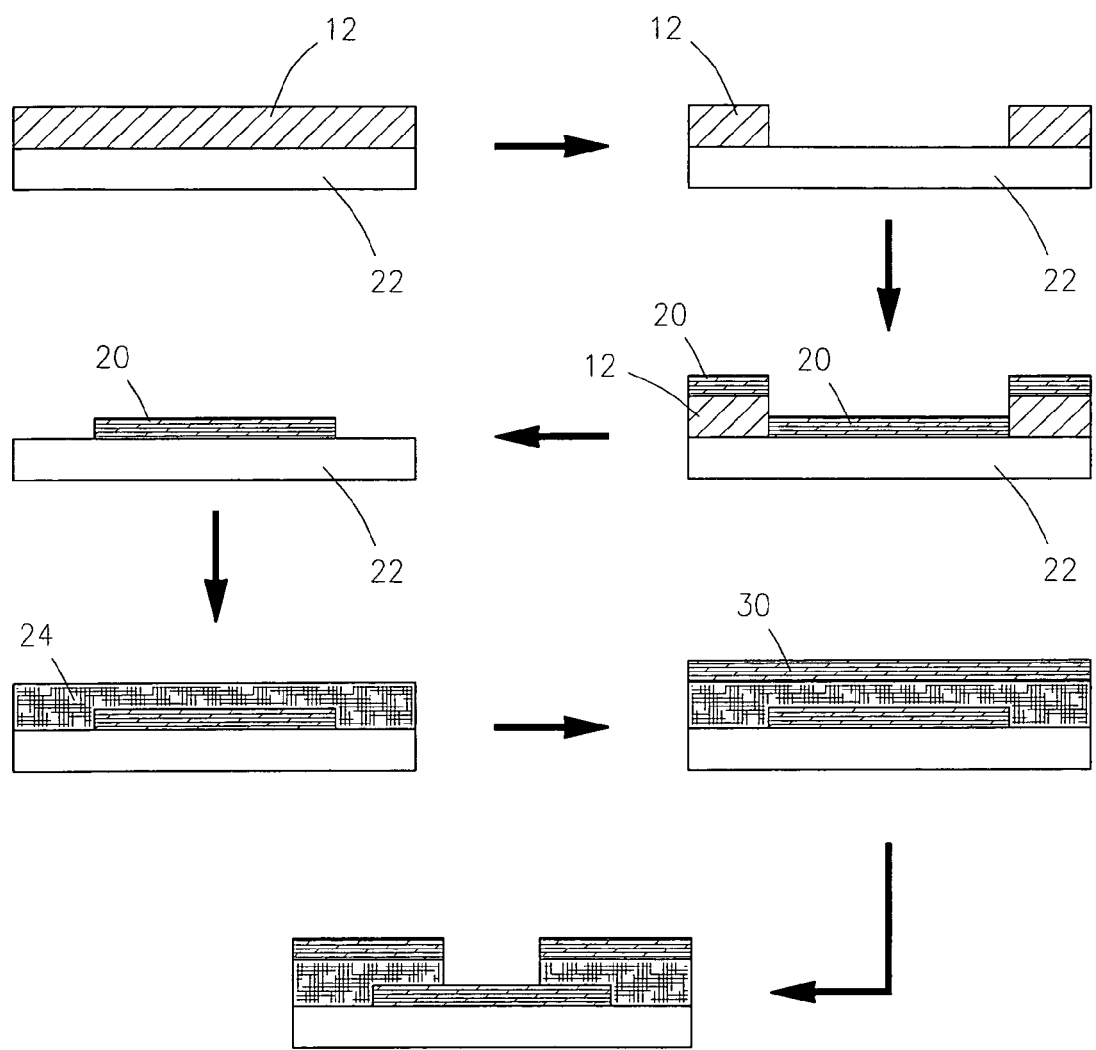
FIG. 20 is a schematic diagram showing a general fabrication process used to construct microcavities having a recessed microdisk electrodes.

The fabrication of RMDs consists of four steps and utilizes both lift-off and etching techniques. The process is shown as a cross-section schematic in FIG. 20. A 2 μm $SiO_2$ film is grown on a Si wafer 22 by thermal oxidation. The wafer is spin-coated with positive photoresist 12 and exposed to UV light (400 W, 300 nm) 16 through a photolithographic mask (HTA Photomask) 10. The photoresist 12 is developed, leaving the pattern of a series of parallel lines, which eventually become the contact leads and microdisk electrodes. A 15 Å Cr film, which serves as an adhesion layer, and 1000 Å Au layer 20 are deposited on the photoresist by thermal evaporation (Edwards 306 Auto). The wafer is sonicated for 15 min in acetone, which dissolves the photoresist, causing lift-off of the metal on top.

After drying for 30 min at 125° C., the wafer is spin-coated with polyimide (4 μm thick) 24. The polyimide 24 is polymerized by exposure to UV light and then cured at 150° C. for 30 min and 250° C. for 30 min to cross-link the polymer. Cr (15 Å) and Au (1000 Å) 30 are deposited on top of the polyimide by thermal evaporation. The wafer is spincoated with positive photoresist. The photoresist is patterned by UV-exposure through a second photolithographic mask (HTA Photomask). The Au and Cr are etched simultaneously with 50% aqua regia (1 $HNO_3$:3 HCl). The remaining photoresist is stripped with acetone and the wafer is dried for 30 min at 125° C. This left a layer of Au/Cr covering the electrode lines with an area over the end of the lines left open for contact purposes.

The wafer is spin-coated with photoresist and patterned using a third photolithographic mask (Photronics). This step leaves a circular opening through the photoresist over each region defined by the lines in the first gold layer. The topmost layer of Au is etched using radio frequency (RF) sputtering (5 min, 50 sccm Ar, 30 mT, 500 V). The polyimide is etched with reactive ion etching (RIE) (13 min, 40 sccm $O_2$, 10 sccm SF, 300 mT, 300 W). Before use, the electrodes are cleaned by sonicating in acetone for 30 s.

Microcavities may be formed in a similar way as shown in FIG. 4. The fabrication of microcavity electrode arrays is accomplished through the use of photolithographic techniques developed for integrated circuit technology. The cavity described here consists of 5 primary layers of material. Layers 1, 3, and 5 are gold, with a Cr adhesion layer, while layers 2 and 4 are polyimide. Layers 1 and 3 serve as the microdisk and nanoband electrodes, respectively. Layer 5 helps maintain the definition of the cavity and prevent tapering during the etching steps. The arrays are generated by depositing and patterning each layer of conductor and insulator. This generated a set of contact lines separated by a sheet of insulator for each electrode. The last step in the fabrication is to create the cavities and expose the microelectrodes using dry etching procedures. Details of fabrication for each layer are listed below.

Layer 1. Both sides of a single crystal silicon wafer are coated with 3 μm of $SiO_2$ at 250° C. by plasma enhanced chemical vapor deposition (PECVD, Plasmatherm, System VII). Alternatively, the $SiO_2$ could be grown on the wafer by thermal oxidation at 650° C. for 8 hours. This served as an initial passivation layer between the electrodes and semi-conductive silicon wafer.

Layers 2 and 4. Wafers are spin-coated with photo-sensitive polyimide (4 μm). The polyimide film is exposed to 350 nm UV light for 12 s through a Karl Suss MA-150 mask aligner to cross-link the polymer leaving a continuous, defect free insulator film. The polyimide is cured at 150° C. for 30 min, followed by 250° C. for 30 min. The wafer is allowed to cool to room temperature before the fabrication continued.

Layer 3. 15 Å Cr and 500 Å Au are deposited by thermal evaporation. The Au thickness of this layer determines the width (w) of the tubular nanoband electrode. The wafer is spin-coated with 4 μm of photoresist. The photoresist is patterned by exposure through a second Cr mask. The Au and Cr are etched simultaneously in 50% aqua regia (3 HCl: 1 $HNO_3$: $4H_2O$). The absence of the ultra-thin Cr layer is verified through resistance measurements with a multimeter. The remaining photoresist is stripped with acetone after the Cr/Au layer had been etched. After rinsing, the wafer is dried for 30 min at 125° C. prior to coating with polyimide.

Layer 5. A top layer of Au is essential to producing cavities with well-defined, vertical walls. Thermal evaporation is used to deposit 25 Å Cr and 1500 Å Au. Photoresist is deposited and patterned according to the procedure for layer 3 using a third Cr mask. The Au and Cr are etched with aqua regia as described above. The remaining photoresist is removed with acetone and the wafer rinsed thoroughly with deionized water.

Cavity Formation. Cavities are created using standard dry etching procedures. The wafer is spin-coated with photoresist (6 μm). The photoresist is patterned by exposure to UV light through a fourth Cr mask. Layer 5 is etched with RF $Ar^+$ sputtering for 5 min and layer 3 for 2 min using a 500 V DC potential with constant pressure (30 mT) and flow (50 sccm) of Ar. The polyimide is etched using reactive ion etching (RIE) with a mixture of $O_2$ (36 sccm) and $SF_6$ (4 sccm) at 300 mT and 300 W RF power for 13 min.

There is a tendency for layers to partially diffuse into adjacent layers. On larger scales this type of diffusion is insignificant. However, because of the extremely small scale of these microcavities, this diffusion can substantially reduce the quality of the microelectrodes. When extremely thin layers are desired, compounds which inhibit diffusion are preferable for the adhesion layers. It may also prove beneficial to incorporate adhesion layers that inhibit diffusion between conducting and insulating layers. Mercaptopropyltriethoxysilane has been shown to reduce diffusion when used in place of chromium as an adhesion layer. However, those skilled in the art will appreciate that a wide variety of compounds may be capable of inhibiting diffusion between layers.

The initial layer of silicate is not necessary when glass is used as the substrate. When silicon is the substrate, only a very thin coating, 2–3 micrometers thick, is required. For other substrates, different initial coatings of different thicknesses may be required depending on the what chemicals are used for the adhesion layer and the photoresist employed.

The chromium adhesion layer may be as little as 15 angstroms thick, but may be as large as desired. Other chemicals may be used as adequate adhesion layers, and the required thickness for these chemicals will vary.

Gold and copper are typically used for the conducting layers. However, any chemical that may be applied to a substrate by thermal evaporation (or alternate methods as and has good conducting qualities may be used. Those skilled in the art of electrochemistry will appreciate that different conducting compounds or elements will be preferred for differing applications of the invention. The deposited conducting layers may be extremely thin, as little as 100 angstroms thick. Although the conducting layers may be as thick as desired, many of the advantages of the invention lie in its microscopic size.

The insulating layers are also extremely thin, less than 3000 angstroms thick. The insulating layers need only be thick enough to prevent the conducting layers from shorting together. It is therefore often desirable to form relatively thick insulating layers. The thicker the insulating layer, the less capacitance there is between the electrodes. Three materials, photosensitive polyimide, $SiO_2$ and $Si_3N_4$ were used as insulators in the disclosed embodiments of the invention. However, any compound may be used so long as it must adequately insulates the conducting layers it is sandwiched between.

Here, the final layer is conducting a conducting layer. The reason for this is that a top layer of gold creates a better defined rim on the cavity. However, an insulator capable of retaining well defined vertical walls would be suitable for a top layer.

Photolithography may also be employed to alter the geometry of a RMD located at the bottom of a microcavity. Instead of being the same shape as the cavity, the microelectrode at the bottom of the well may be linear, stretching across the diameter of the cavity. It may also be designed to only cover one half of the bottom of the well. Any number of patterns may be used for the microelectrode at the base of the cavity by simply modifying the mask used during photolithography of the first layer.

Micropores may be created in addition to microcavities. Multiple electrodes can be fabricated in arrays of micropores using the alternating layer method. An advantage of having two or more electrodes within the same small region is for the purpose of performing self-contained electrochemical analysis on small samples. Construction of microcavities can follow microfabrication techniques which involve many steps and sophisticated masks, and construction of micropores in a flexible polyimide substrate can involve a low-technology approach.

Although the microstructures described here are all circular having diameters, those skilled in the art will understand that any geometry may be used. These microsctures my have a polygon shape, such as a square or rectangle. The shape of the microstructures is easily changed by adjusting the shape of the masks used in the making of the microstructures.

Amino acid analysis in alkaline solutions was demonstrated with a microcavity device with a copper tubular nanoband (TNB) electrode. Self-contained electrochemistry at the microcavity devices of small volumes and analysis in flowing solutions for amino acid detection holds promise, but materials stability issues still need to be addressed. Arrays of multi-electrode micropores and their characterization are described. Preliminary results at micropores show that small volume analysis is possible and that advantages over the microcavities include multiple drop analysis. The flexible substrate makes it more useful in locations that are not suitable for rigid electrochemical devices and the pores should be useful in flow-through detector applications. Addition of a third electrode layer and formation of a reference electrode should improve performance in small volume analysis. In both the microcavity and micropore systems, the addition of subsequent layers of insulator and conductor can increase the numbers of electrodes used in small volume experiments as well as the functionality of the device.

Microcavity electrodes support currents that can be measured using conventional electrochemical equipment and electrochemical equipment with current amplifiers. These microcavities and micropores are readily adapted to existing monitoring, detecting and experimental techniques.

Flux of solution species to small electrodes is dominated by radial diffusion, resulting in a high flux per unit area. Consequently, microelectrodes can be fouled readily. The electrodes can be cleaned by electrochemically cycling the potential several times. This is a common method to clean electrodes without requiring direct contact with substances like polishing cloths and polishing compounds.

Electrodes within the cavities are located very close to each other. Thus, electrochemical products generated at one electrode may be collected or interfere with the electrochemistry of another. The time scales of the experiments can be controlled to avoid this problem. Also, care can be taken so that electrogenerated products are irreversible and no longer electroactive for interference with adjacent electrodes. The close proximity of the electrodes also has advantages. Redox species may be rapidly recycled and therefore used to amplify current.

Listed below are a series of examples in which the present invention was reduced to practice. These exemplify only a small percentage of the possible embodiments, but represent typical constructions of the invention.

EXAMPLE 1

Microfabricated recessed microdisk electrodes (RMDs) of 14 and 55 µm diameter were constructed. For evaluation of electrode function, both faradaic current in $Ru(NH_3)_6^{3+}$ solution and charging current in $KNO_3$ solution were measured with cyclic voltammetry (CV). At slow scan rates (0.1 $Vs^{-1}$), where radial diffusion dominates, the steady state measured with 55 µm RMD is 53.5±0.48 nA and the 14 µm RMD is 5.39±0.96 nA. At fast scan rates (204 $Vs^{-1}$), where linear diffusion dominates, the current measured with the 55 µm RMD is 784.6±42.0 nA and the 14 µm RMD is 35.4±9.5 nA. The dependence of capacitance on scan rate of the RMDs was found to be similar to that of a macroelectrode, indicating good adhesion between the insulator and the electrode. The signal-to-noise ratio of the RMD compared to a planar disk microelectrode (PDM) is on average 4 times greater for both of the stirred solutions.

All chemicals are reagent grade and used as received. Aqueous solutions are prepared with high purity deionized water (Milli-Q, model RG). A gold coin (Credit Suisse, 99.99%) and chromium plated tungsten rod (R. D. Mathis) served as sources for thermal evaporation. Silicon wafers (5", (100)) were obtained from Silicon Quest International (Santa Clara, Calif.). Potassium nitrate, sulfuric acid, hydrochloric acid, nitric acid and 30% hydrogen peroxide were purchased from Fisher Scientific. Hexaamineruthenium(III) chloride is obtained from Aldrich Chemical Co. Positive photoresist (AZ433ORS) and photoresist developer (AZ400K) were purchased from Hoechst-Celanese. Polyimide (Pyralin PI-2721, DuPont) is purchased from DuPont. A gold 10 µm diameter PDM (BioAnalytical Systems, BAS) is used as the control.

The fabrication of RMDs is accomplished by forming a hole through a Au and polyimide layer exposing an underlying Au disk. FIG. 5 shows a cross-section view of an RMD. The top layer of Au, while not used in the electrochemical measurements is essential in the fabrication process so that cavities with well-defined, vertical walls can be produced. Cavity devices, that accommodate two individually-addressable electrodes, are described elsewhere. The focus here is on the use of the same design for a more simplified electrode configuration.

The fabrication of RMDs consists of four steps. The process is shown as a cross-section schematic in FIG. 20. A 2 µm $SiO_2$ film is grown on a Si wafer by thermal oxidation. The wafer is spin-coated with positive photoresist and exposed to UV light (400 W, 300 nm) through a photolithographic mask (HTA Photomask). The photoresist is developed, leaving the pattern of a series of parallel lines, which eventually become the contact leads and microdisk electrodes. A 15 Å Cr film, which serves as an adhesion layer, and 1000 Å Au layer are deposited on the photoresist by thermal evaporation (Edwards 306 Auto). The wafer is sonicated for 15 min in acetone, which dissolves the photoresist, causing lift-off of the metal on top.

After drying for 30 min at 125° C., the wafer is spin-coated with polyimide (4 µm thick). The polyimide is polymerized by exposure to UV light and then cured at 150° C. for 30 min and 250° C. for 30 min to cross-link the polymer. Cr (15 Å) and Au (1000 Å) are deposited on top of the polyimide by thermal evaporation. The wafer is spin-coated with positive photoresist. The photoresist is patterned by UV-exposure through a second photolithographic mask (HTA Photomask). The Au and Cr are etched simultaneously with 50% aqua regia (1 $HNO_3$:3 HCl). The remaining photoresist is stripped with acetone and the wafer is dried for 30 min at 125° C. This left a layer of Au/Cr covering the electrode lines with an area over the end of the lines left open for contact purposes.

The wafer is spin-coated with photoresist and patterned using a third photolithographic mask (Photronics). This step leaves a circular opening through the photoresist over each region defined by the lines in the first gold layer. The topmost layer of Au is etched using radio frequency (RF) sputtering (5 min, 50 sccm Ar, 30 mT, 500 V). The polyimide is etched with reactive ion etching (RIE) (13 min, 40 sccm $O_2$, 10 sccm SF, 300 mT, 300 W). Before use, the electrodes are cleaned by sonicating in acetone for 30 s. The electrode pattern design includes 4 lines of Au underlying the polyimide. Each has one cavity of a different nominal diameter: 50 µm, 10 µm, 5 µm, and 2 µm. Only the 50 and 10 µm cavities could be formed with this set of microfabrication conditions. Scanning electron microscopy (SEM) is performed with a Hitachi S-2300 scanning electron microscope (20 kV accelerating voltage). A profilometer (Dektak 3030) is used to measure the polyimide thickness. The average diameter of the small RMDs is 14±0.28 µm (n=3 cavities). The average diameter of the large RMDs is 55.2 µm±0.0 (n=3 cavities).

The depth of the cavities is not measured directly. The small diameter of the cavity prevented the use of atomic force microscopy or a profilometer. To obtain an approximate measure of the depth, the thickness of the polyimide layer is measured after patterning using a profilometer. The thickness of the polyimide is consistently 4 µm.

Cyclic voltammetry is used to characterize the electrochemical response of the RMDS. $Ru(NH_3)_6^{3+}$ is chosen as a probe because of its well-established electrochemical properties.[237] A 10 µm PDM is used for comparison.

CV responses from the 10 µm PDM (a) and the 14 µm (b) and 55 µm (c) RMDs were obtained in 5.0 mM $Ru(NH_3)_6^{3+}$ and 0.5 M $KNO_3$ at 0.1 $Vs^{-1}$. At this scan rate, none of the microelectrodes exhibit true steady-state behavior. The 10 µm PDM is the closest, while the 55 µm RMD is the furthest from this behavior. The deviation occurs for two reasons. As electrode size increases, the contribution of linear diffusion to the total flux for a given time scale increases. This is the case in comparing CV responses from the 14 and 55 µm RMDs. Secondly, the walls of the cavity prevent radial diffusion from occurring as long as the diffusion layer is within the cavity. This is demonstrated by comparing CV responses of the 10 µm PDM and the 14 µm RMD.

For the 55 µm RMD, steady state current persists to a scan rate of 0.1 $Vs^{-1}$. The steady state current for the 55 µm RMD is 53.50±0.48 nA. At faster scan rates, the current increases with scan rate in a fashion like that predicted for linear diffusion. At 204 $Vs^{-1}$, where the diffusion layer is thin and the electrodes should follow theory for linear diffusion (Eq. 5), the maximum current is 784.6±41.2 nA.

For the 14 µm RMD, steady state current persists up until 1 $Vs^{-1}$ is reached. Above this scan rate, the current increases with increasing scan rate. At 204 $Vs^{-1}$, the current measured at the 14 µm RMDs is 35.37±9.51 nA. There is no apparent transition region between steady state and linear models for this size of RMD.

Capacitance studies are used to evaluate the quality of the construction of the microelectrodes. Usually, the capacitance is considered to be independent of scan rate. However, even at the macroelectrode level this is not the case. The slope for the RMDs is similar to that of the macroelectrode, indicating that the seal between the insulator and electrode is good, and no cracking has occurred.

The 14 µm RMDs are excellent candidates for electrochemical detectors in convective systems because the decrease in Signal to Noise Reduction is minimal with increasing convection as compared to planar disk microelectrodes.

EXAMPLE 2

Construction and characterization of an electrochemical cell containing two individually-addressable microelectrodes, a disk and a nanoband are described. The diameter of the cell is 53 µm and the depth 8 µm. The RMD and TNE separated vertically by 4 µm. Both electrodes are evaluated using cyclic voltammetry in $Ru(NH_3)_6^{3+}$ and electrolyte. The faradaic response is compared with theories for radial and linear diffusion for both geometries. The response of the recessed disk microelectrodes (RMD) is compared to previous work[211] to evaluate the effects of depth of the response. Capacitance as a function of scan rate for both microelectrodes is compared to a macroelectrode to determine the quality of construction.

All chemicals are reagent grade and used as received. Aqueous solutions are prepared with high purity deionized water (Milli-Q). A gold coin (Credit Suisse, 99.99%) and chromium plated tungsten rod (R. D. Mathis) served as sources for thermal evaporation. Silicon wafers (5", (100)) are donated by the High Density Electronics Center at the University of Arkansas. Potassium nitrate, sulfuric acid, and 30% hydrogen peroxide are obtained from Fisher Scientific. Hexaamineruthenium(III) chloride is purchased from Aldrich Chemical Co. Positive photoresist (AZ4330RS) and photoresist developer (AZ400K) are obtained from Hoechst-Celanese. Photodefineable polyimide (Pyralin PI-2721) is purchased from DuPont.

The fabrication of microcavity electrode arrays is accomplished through the use of photolithographic techniques developed for integrated circuit technology. The cavity reported here consists of 5 primary layers of material. Layers 1, 3, and 5 are gold, with a Cr adhesion layer, while layers 2 and 4 are polyimide. Layers 1 and 3 serve as the microdisk and nanoband electrodes, respectively. Layer 5 helps maintain the definition of the cavity and prevent tapering during the etching steps. The arrays are generated by depositing and patterning each layer of conductor and insulator. This generated a set of contact lines separated by a sheet of insulator for each electrode. The last step in the fabrication is to create the cavities and expose the microelectrodes using dry etching procedures. Details of fabrication for each layer are listed below.

Layer 1. Both sides of a single crystal silicon wafer are coated with 3 µm of $SiO_2$ at 250° C. by plasma enhanced chemical vapor deposition (PECVD, Plasmatherm, System VII). Alternatively, the $SiO_2$ could be grown on the wafer by thermal oxidation at 650° C. for 8 hours. This served as an initial passivation layer between the electrodes and semiconductive silicon wafer. Layer 1 is patterned using a lift-off procedure as described above.

Layers 2 and 4. Wafers are spin-coated with photosensitive polyimide (4 µm). The polyimide film is exposed to 350 nm UV light for 12 s through a Karl Suss MA-150 mask aligner to cross-link the polymer leaving a continuous, defect free insulator film. The polyimide is cured at 150° C. for 30 min, followed by 250° C. for 30 min. The wafer is allowed to cool to room temperature before the fabrication continued.

Layer 3. 15 Å Cr and 500 Å Au are deposited by thermal evaporation. The Au thickness of this layer determines the width (w) of the tubular nanoband electrode. The wafer is spin-coated with 4 µm of photoresist. The photoresist is patterned by exposure through a second Cr mask. The Au and Cr are etched simultaneously in 50% aqua regia (3 HCl: 1 $HNO_3$: $4H_2O$). The absence of the ultra-thin Cr layer is verified through resistance measurements with a multimeter. The remaining photoresist is stripped with acetone after the Cr/Au layer had been etched. After rinsing, the wafer is dried for 30 min at 125° C. prior to coating with polyimide.

Layer 5. A top layer of Au is essential to producing cavities with well-defined, vertical walls. Thermal evaporation is used to deposit 25 Å Cr and 1500 Å Au. Photoresist is deposited and patterned according to the procedure for layer 3 using a third Cr mask. The Au and Cr are etched with aqua regia as described above. The remaining photoresist is removed with acetone and the wafer rinsed thoroughly with deionized water.

Cavity Formation. Cavities are created using standard dry etching procedures. The wafer is spin-coated with photoresist (6 µm). The photoresist is patterned by exposure to UV light through a fourth Cr mask. Layer 5 is etched with RF $Ar^+$ sputtering for 5 min and layer 3 for 2 min using a 500 V DC potential with constant pressure (30 mT) and flow (50 sccm) of Ar. The polyimide is etched using reactive ion etching (RIE) with a mixture of $O_2$ (36 sccm) and $SF_6$ (4 sccm) at 300 mT and 300 W RF power for 13 min.

The initial characterization of the cavity microelectrode system is performed with scanning electron microscopy (SEM). The diameter of the cavity is 53 µm. SEM shows a cavity opening that is uniform and smooth. Only the protective Au of layer 5 and the disk microelectrode (layer 1) can be seen. A "halo" can be seen in layer 5. This is caused by partial exposure of layer 5 during the second RF sputtering step resulting in partial removal (the topmost 100's of Å) of Au where the photoresist has thinned around the rim of the cavity.

Cyclic voltammetry is used to evaluate the electrochemical response of the recessed microdisk (RMD) and tubular nanoband electrode.

Recessed Microdisk Electrode. In the present application, the RMDs are 8 µm deep (instead of 4 µm). At slow scan rates, the current follows radial diffusion theory. The experimental current (measured at 0.1 $Vs^{-1}$) is 36.65±5.1 0 nA. The RMDs maintain steady state behavior to 0.25 $Vs^{-1}$. At fast scan rates (>0.25 $Vs^{-1}$), the current increases, but does not follow predictions based upon linear diffusion models. For example, at 204 $Vs^{-1}$ the $i_{max}$ is 566.9±133.7 nA, which is substantially less than the theoretically calculated current, 1168 nA.

The quality of the fabrication is evaluated from capacitance values. Capacitance is calculated from the charging current obtained from CV experiments in pure electrolyte (0.5 M $KNO_3$). The capacitance will have a large dependence upon scan rate if there is poor adhesion between the insulator and electrode or if there is cracking in the insulator around the electrode. The capacitive density is calculated and compared to a Au macroelectrode.

Ideally, the capacitance should be independent of scan rate, however, the macroelectrode, which has no insulator, has a dependence. The scan rate dependence of both microelectrodes is close to that for the macroelectrode and is similar to that seen previously for the RMDs.[211] This indicates that there is a good seal between the insulator and electrode and there is little or no cracking.

EXAMPLE 3

This example illustrates how microcavities may be modified in order to form troughs having electrodes on either side. They retain the small dimensions regarding height and width, but have macroscopic length.

All reagents (Aldrich) were reagent grade and were used without further purification, unless otherwise specified. Deionized (DI) water was prepared using an ultrapure water system (Millipore, France model Milli Q RG). Sulfuric acid, hydrogen peroxide, iso-propanol were electronic grade (J. T. Baker). A cold coin (Canadian Maple Leaf, 99.9%) and chromium-plated tungsten rods (R. D. Mathis) were used as sources for thermal evaporation. For photolithography, HR 200 negative photoresist, WNRD negative resist developer, PF thinner and universal photoresist stripper Nophenol (OCG Microelectronic Materials, Inc.) were used.

Deposition of Chromium, Gold and Silicon Nitride. Glass slides (Fisher Scientific) were cut to 1 in.×1 in. and cleaned with a 7:3 (v/v) solution of concentrated $H_2SO_4$ and 30% $H_2O_2$, for 15 min, thoroughly rinsed with DI water, dried with a strong flow of $N_2$, and oven dried at 110° C. for 10 min. Cleaned slides were coated with ~20/Å of chromium, followed by layers of different thicknesses (~100 Å, 250 Å, 350 Å, 500 Å, 750 Å, 1000 Å) of gold produced by thermal metal vapor deposition with an Edwards E306A coating system. Thicknesses were estimated by a piezoelectric thickness monitor. Following gold deposition, a layer of silicon nitride (approximately 3000 Å) was deposited using a gas mixture of 20 sccm monosilane, 80 sccm ammonia, and 200 sccm nitrogen (1 hr). Silicon nitride deposition was done in a parallel plate, capacitively coupled, 13.56 MHz rf plasma enhanced chemical vapor deposition system (Texas Instruments model A24C).

Atomic Force Microscopy (AFM). Contact AFIM was used for studying topography of metal and insulator layers, and also for measuring film thicknesses (Digital Instruments, CA model Nanoscope III). The tip and cantilevers used were made of silicon nitride and purchased from Digital Instruments, CA. Samples for topography study were prepared by vapor deposition as described in the deposition section above. Film thickness measurements were made on electrode array contact pads.

Microfabrication. After deposition of metal and insulator layers, the slides were spin-coated (Headway Research Inc., Spinner Model 1-EC 101-R485) with negative photoresist at 2000 rpm for 30 s, and exposed to UV light through the array mask using a mask aligner (Quintel Corporation, Model Q-404) for 6 s. The array pattern was developed on substrates using negative photoresist developer for 135 s, rinsed in thinner for 15 s followed by an iso-propanol rinse, dried with a strong flow of $N_2$ and oven-baked at 135° C. for 30 min. Silicon nitride, gold and chromium were etched away by RIE using a Plasma Therm Model 520, parallel-plate etcher. The gas mixtures used were $CF_4$ (46 sccm) for silicon nitride (RF power 200 W, pressure 300 mTorr), $CF_4$ (31 sccm)+$CCl_4$ (49 sccm) for gold and chromium (RF power 450 W, pressure 150 mTorr) based on procedure reported by Ranade et al.[176] After RIE, the photoresist was removed using universal photoresist stripper Nophenol. The arrays were cleaned to remove organic residues by either $O_2$ plasma etching (RF power 450 W, pressure 700 mTorr for 15 min) or by soaking in a solution of 7 ml of conc. $H_2SO_4$+3 ml of 30% $HO_2$+1O ml DI water for 5 min, followed by rinsing thoroughly with DI water, and drying in an oven at 110° C. for 1O min. A schematic representation of the fabrication procedure is shown in FIG. 4.

Scanning Electron Microscopy (SEM). SEM was used to get the images of electrode array after fabrication.

Electrochemical Experiments. Cyclic voltammetry (CV) was performed using one of the two computer-interfaced potentiostats, a Bioanalytical Systems, Model 100B, with BAS 100W software or a Pine Instrument Company Bipotentiostat, Model AFCBPI, with Cyclic Voltammetry Module software (beta release). In some experiments a low current amplifier (Bioanalytical Systems, Model PA1) was used. The reference was an aqueous Ag/AgCl (saturated KCl) electrode. A platinum gauze was used as an auxiliary electrode. Cyclic voltammograms were obtained for one of the two solutions, 0.5 mM potassium ferricyanide or 5.00 mM hexaammine ruthenium (III) chloride. The electrolyte used was 0.50 M $KNO_3$.

Gold Thickness Measurements. Gold film thicknesses were measured by X-Ray reflectivity, surface profilometer (Sloan Dektak 3030) and AFM; in addition to the piezoelectric thickness monitor on the coating system. Table 1 shows the thicknesses as measured by various techniques.

TABLE 1

THICKNESS MEASUREMENTS

| Piezoelectric crystal, nm | Profilometer, (Dektak 3030) | X-ray reflectivity, nm | AFM, nm |
|---|---|---|---|
| 10 | — | 25.7 + 2.3 | — |
| 25 | — | — | 37.0 + 2.0 |
| 35 | — | — | — |
| 50 | — | — | 77.7 + 3.7 |
| 75 | — | — | 125.7 + 5.3 |
| 100 | 130.5 + 6.0 | — | 143.5 + 9.6 |

Topography of thin cold films on glass. Topography of gold layers plays an important role in determining the geometry of the fabricated band electrodes. Less variation in surface roughness will give a better defined band geometry. Contact mode atomic force microscopy (AFM) of different film thicknesses of gold on glass with chromium as an adhesion layer revealed that the topography depends upon the film thickness. As increasingly thicker layers of gold were examined, topography evolved from uniformly distributed islands of gold ranging from about 20 nm in diameter (parallel to the substrate surface) for 100 Å gold, to ~40 nm for 500 Å gold, to 60–100 nm for 1500 Å gold. By comparing % RMS roughness with the thickness of the gold layers we can see that as we go to larger electrode widths we have better defined band geometry. Silicon nitride topography indicates that, due to its relatively smoother surface structure, it can provide a planarizing layer for subsequent gold layer deposition.

Comparison of a step and a band electrode. The layering technique used for making the submicron band electrodes is an effective way of increasing the functionality per unit area by building alternate layers of conductor and insulators with at least two conductor layers. It is important for this purposes that, comparison of current response for electrodes with and without insulator layer on top be made so that the feasibility of building more than one conductor layer be tested. An electrode array without a silicon nitride layer on top was constructed using the same procedure as for the two layer array. Electrodes prepared in this manner are called step electrodes. Gold film thickness was the same for both these electrodes. As can be seen from the magnitude for current at step and band electrodes we do not lose as much response as is evident from surface area calculations (insulator layer on top covers 98% of the total area). Another factor that needs to be looked at carefully for this comparison is the integrity of the silicon nitride layer and it's insulating properties.

Voltammetric Behavior. Voltammetric electrodes with edge band geometry show voltammetric responses due to non-linear diffusion at slower scan rates. This is indicated by sigmoidal shaped cyclic voltammograms at slower scan rates. At higher scan rates, linear diffusion predominates and voltammograms become peak shaped. Scan rate study for other electrode widths indicates that, as the electrode width is increased the peak shaped voltammograms appear at a lower scan rate and vice versa.

Limiting Current. For a hemicylindrical electrode, the limiting current at long time is given by equation 1, derived by Kovach et al.[30] based on the expression derived by Jaeger⁻ radial flux to a hemicylindrical solid boundary.

$$i(t) = 2nFDlC^b X/\ln[4Dt/r_0^2] \quad (1)$$

Here, D is the diffusion coefficient, F is Faraday's constant, l is the electrode length, $C^b$ is the concentration of redox species in bulk solution, t is time and $r_0$ is the effective electrode radius. It has been shown by Szabo et al[32] that long time current for a band electrode of width w is equal to that for a hemicylindrical electrode with radius w/4.

TABLE 2

Gold Thickness Measurements

| Piezoelectric crystal, nm | Profilometer, (Dektak 3030) nm | X-ray reflectivity, nm | AFM, nm |
|---|---|---|---|
| 10 | — | 25.7 ± 2.3 | — |
| 25 | — | — | 37.0 ± 2.0 |
| 35 | — | — | — |
| 50 | — | — | 77.7 ± 3.7 |
| 75 | — | — | 125.7 ± 5.3 |
| 100 | 130.5 ± 6.0 | — | 143.5 ± 9.6 |

EXAMPLE 4

The characterization and application of a cavity electrode system (CES) containing individually-addressable recessed microdisk and tubular nanoband electrodes is discussed. Two diameters of CES, 13 and 53 µm, are described. The depth of each cavity is 8 µm. Each of the electrodes is characterized in Ru(NH$_3$)$_6^{3+}$ and KNO$_3$ solution at 0.1 Vs$^{-1}$. The experimental current measured at the electrodes in the 53 µm CES were within error of models for radial diffusion to the respective geometry. The experimental current for both electrodes in the 13 mm CES deviated from the models. The band electrode exceeded the model (6.31±0.28 nA compared to 3.98 nA). The disk electrode was less than the model predicted (2.13±0.46 nA compared to 3.81 nA). The formation and stability of a Ag/AgI pseudo reference electrode on the band electrode is shown.

The $E_o$ for Ru(NH$_3$)$_6^{3+}$ measured with the Ag/AgCl electrode is −0.053±0.016 V. The reference electrode was found to be stable over multiple experiments without supporting electrolyte. The complete electrochemical cell was used for analysis in small volumes (1 and 10 µL) of hydroquinone and Ru(NH$_3$)$_6^{3+}$. Finally, the CES was used in stirred solutions. The signal-to-noise ratio (SNR) from 13 µm CES showed no dependence upon stir rate up to 150 rotations per minute (rpm). The SNR from the 55 µm CES showed only a small change with stir rates up to 150 rpm.

All chemicals were reagent grade and used as received. Aqueous solutions were prepared with high purity deionized water (Milli-Q, model RG). A gold coin (Credit Suisse, 99.99%) and a chromium plated tungsten rod (R. D. Mathis) served as sources for thermal evaporation. Silicon wafers (5", 100) were donated by the High Density Electronics Packaging Facility, University of Arkansas. Potassium nitrate, sulfuric acid, hydrochloric acid, silver nitrate, potassium iodide, sodium thiosulfate, nitric acid and 30% hydrogen peroxide were purchased from Fisher Scientific. Hexamineruthenium(III) chloride and hydroquinone were obtained from Aldrich Chemical Co. Positive photoresist (AZ433ORS) and photoresist developer (AZ400K) were purchased from Hoechst-Celanese. Polyimide (Pyralin PI-2721, DuPont) was purchased from DuPont.

The fabrication of the cavity electrode system (CES) has been described previously. In brief, the CES is made by depositing and patterning alternating layers of Au and polyimide on an oxidized Si wafer, with a total of five layers. Layers 1, 3, and 5 are Au, with a Cr adhesion layer. Layers 2 and 4 are a polymeric insulator, polyimide. After these layers have been deposited and patterned, a cavity is etched through the top 4 layers, exposing a 500 Å wide tubular nanoband electrode (TNE) and a recessed microdisk electrode (RMD). Two diameters of cavity are reported here, 13 µm and 53 µm. Both cavities are 8 µm deep.

Electrochemical Measurements

A BAS-100B potentiostat and PA-1 preamplifier controlled with BAS-100W electrochemical software were used to perform cyclic voltammetry (CV) and chronoamperometry (CA). For characterization experiments, a Pt flag auxiliary and macro Ag/AgCl (sat'd KCl) reference electrode were used to complete the three electrode system. Stirring studies involved CA and were performed on a Corning PC-320 stir plate with a ½" magnetic stir bar (Fisher Scientific). The cell volume was 40 mL and was not purged prior to CA. The rotation rate was determined by counting the rotations of the stir bar over a given time period.

Microreference Formation

Formation of a Ag/AgI pseudoreference microelectrode was accomplished following the procedure developed by Bratten et al. Ag was deposited for 1 s on the TNE at −0.5 V versus a Pt flag from a solution containing the complex ion [AgI$_2$]$^-$K$^+$. The complex ion was obtained in a solution of 0.1 M AgNO$_3$, 1 M KI, and 0.25 mM Na$_2$S$_2$O$_3$. The Ag was oxidized in saturated KI for 0.5 s at +0.5 V versus a Pt flag. After formation of the reference electrode, the electrodes were rinsed thoroughly with deionized water, dried, and stored in a covered vial. Stability of the Ag/AgI pseudoreference was determined using cyclic voltammetry in 5.0 mM Ru(NH$_3$)$_6^{3+}$ and 0.5 M KNO$_3$, solution. The $E^0$ potential was compared to the potential determined using a macro Ag/AgCl (sat'd KCl) reference electrode.

Small Volume Analysis

The application of the CES to measurement of electroactive species in small volumes was accomplished using the Ag/AgI pseudoreference and layer 5 as the auxiliary electrode. A small volume of solution was placed on the cavity using an automatic pipette. Two solutions were tested using the CES. A 5.0 mM RU(NH$_3$)$_6^{3+}$/0.5 M KNO$_3$ solution was used as the model system because of its well understood properties. The second analyte tested was hydroquinone. A 4.0 mM solution in 0.5 M $KNO_3$ solution buffered to pH 6.60 with 0.05 M phosphate buffer was analyzed.

Convection Studies

Convection studies were carried out using both diameters of CES. The internal reference and auxiliary electrodes were used. The protocol used for testing electrodes in convective systems has been reported previously. In brief, a solution of either 5.7 mM $Ru(NH_3)_6^{3+}$ and 0.5 M $KNO_3$ or 1.0 mM hydroquinone in pH 6.60 phosphate (0.05 M) buffer was placed in a cell containing a ½' magnetic stir bar. The electrodes were tested in both static solution and solution stirred at either 70 or 150 rotations per minute (rpm). Chronoamperometry (CA) was used to determine the effect of convection on faradaic current. For the $Ru(NH_3)_6^{3+}$, the potential was stepped from +0.2 V to −0.4 V vs Ag/AgI for 5 s. For the hydroquinone, the potential was stepped from +0.2 V to +0.75 V vs Ag/AgI for 5 s.

3. Results and Discussion

The cavity electrode system (CES) was evaluated using cyclic voltammetry (CV) in $Ru(NH_3)_6^{3+}$ and 0.5 M $KNO_3$ solution. Cavities of two different diameters, 53 and 13 μm, were compared with models presented for each electrode geometry. The CES contains two electrodes, a tubular nanoband electrode (TNE) and a recessed disk microelectrode (RMD).

At slow scan rates, the RMD in a 53 μm cavity has been shown previously to follow the model for radial diffusion to a planar microdisk electrode (PMD), while the RMD in a 13 μm cavity follows the model for radial diffusion to a RMD. The steady state current measured for the 53 μm RMD is 39.5±2.93 nA which matches closely with the predicted current (39.9 nA). The steady state current for the 13 μm RMD is 2.13±0.46 nA which is less than the predicted current (3.81 nA).

The electrochemical behavior of the TNE in a 53 μm diameter cavity has been described[2,10] and found to follow models for radial diffusion to a band electrode.[30] The comparison of a TNE to models for radial diffusion to a band electrode in a 13 μm cavity has not been reported. At 0.1 $Vs^{-1}$, the experimental current for the TNE in a 53 μm cavity is 25.8±4.2 nA, which matches with the predicted current (16.2 nA). For the TNE in a 13 μm cavity, the experimental current is 6.31±0.28 nA, which is greater than the predicted current (3.98 nA).

Formation and Stability of Ag/AgI Pseudoreference

The ability to make accurate potential measurements in small volumes of samples requires the presence of a reference electrode. Bratten et al. {Cooper} have reported the use of a Ag/AgI pseudoreference microelectrode for small volume measurements. Ag/AgI was deposited on the TNE and CV in 5.0 mM $Ru(NH_3)_6^{3+}$ and 0.5 M $KNO_3$ was used to characterize the system. Layer 5 was used as the auxiliary electrode to complete the electrochemical system. The standard reduction potential of AgI is −0.1 519 V vs the normal hydrogen electrode (NHE) as compared to AgCl at +0.2223 V vs NHE. The experimentally determined reduction potential of $Ru(NH_3)_6^{3+}$ vs Ag/AgCl (sat'd KCl) is −0.16±0.002 V, but −0.053±0.016 V vs the micro-Ag/AgI pseudoreference. The redox potential of $Ru(NH_3)_6^{3+}$ vs Ag/AgI, predicted by standard reduction potentials, should be +0.222 V. The 0.275 V shift in reference potential is probably due to the lack of supporting electrolyte solution.

After determining that the reference potential of the Ag/AgI pseudoreference electrode was more positive than predicted, a study was done to determine if the electrode was stable over time with multiple experiments. A simple study was done to determine the reliability of the Ag/AgI electrodes from run to run. A 53 μm cavity was placed in 5.0 mM $Ru(NH_3)_6^{3+}$ and 0.5 M $KNO_3$ solution and 10 CVs collected at 0.5 $Vs^{-1}$, allowing the system to go to open circuit between each cycle. The 53 μm cavity was chosen because the RMD draws more current than the TNE and therefore, the microreference in the 53 μm cavity should be less stable than the 13 μm CES. The $E^0$ potential does not change between runs indicating that the pseudoreference electrode is stable in the absence of supporting $I^-$ ions.

Small Volume Analysis

The application of the CES to small volume analysis was first demonstrated with $Ru(NH_3)_6^{3+}$ as the analyte. The response of the working electrode in these two volumes is essentially identical. The experimental current is 2.89±0.53 nA for the 10 μL sample and 2.67±0.46 nA for the 1 μL sample. $E^0$ for the 10 μL sample is −0.086±0.034 V and for the 1 μL sample is −0.123±0.063 V.

The second small volume system tested was hydroquinone. Hydroquinone is a common moiety in pharmaceuticals and biological compounds. The current for the two samples is within error, 2.91±0.84 nA for the 10 μL and 2.58±0.72 nA for the 1 μL.

Convection Studies

Both diameters of CES were tested in stirred solutions to demonstrate the advantageous nature of RMDs in convective systems. RMDs with a 14 μm diameter were found to provide a 4 fold improvement in signal-to-noise ratio (SNR) over planar microdisk electrodes (PMDs).

To obtain an accurate measure of the effects of convection on the faradaic current, chronoamperometry (CA) was used. The potential was stepped from a region of non-faradaic current transfer to a region of either oxidation (hydroquinone) or reduction ($Ru(NH_3)_6^{3+}$). No data smoothing was employed and a lowpass filter with cutoff frequency of 2500 Hz was used to minimize electrical noise. The potential was stepped from 0.0 V to +0.6 V vs Ag/AgI for 5 s. The signal-to-noise ratio (SNR) was calculated by first determining the steady state current between the 1st and 5th s of the potential step. The current was then divided by the standard deviation of the data during the same time duration. The noise present in the static solution is due to electrical noise. The SNR in static solution is 9.85±1.8. The SNR in a solution stirred at 70 rpm is 8.37±0.86 and at 150 rpm is 8.99±2.20. All three of these fall within error of each other.

EXAMPLE 5

Analytical separation techniques such as high performance liquid chromatography, microfluidic lab-on-a-chip technology and capillary electrophoresis require a detector to measure the concentration of analyte in the eluant. The microcavity devices that are described here were modified from those described above for the purpose of detecting amino acids by replacing the middle Au layer with one of Cu. The Cu layer forms a tubular nanoband (TNB) electrode around the walls of the cavity. Copper was chosen because of previous success by Baldwin and coworkers with electrochemical detection at electrodes of this metal of amino acids in alkaline solutions. High performance liquid chromatography systems have employed copper macroelectrodes as electrochemical detectors. In capillary electrophoresis, copper microwire electrodes have been used to detect nanomolar quantities. The microcavity electrodes that are reported here could potentially be used in these kinds of separations systems. In the present study, electrode pretreatment and conditions to detect alanine, aspartic acid, glycine, histidine, lysine, and serine in NaOH solutions were established at a vapor-deposited copper macroelectrode on a silicon wafer. Detection of serine by Cu TNB electrodes in microcavity devices are compared to macroelectrode results.

Direct detection of amino acids may be carried out via a catalytic oxidation mechanism which occurs in alkaline aqueous solution at copper electrodes at 688 mV vs. Ag/AgCl (sat'd KCl). Copper nano-electrodes have been constructed in microcavities for the purpose of electrochemical detection of amino acids in turbulent solutions. The cavity is intended to reduce noise due to variations in convection, the microelectrodes are to allow faster measurements to be made in a small volume. Studies are first described relating to macroelectrodes which were performed to define guidelines for optimum NaOH concentration (0.1 M NaOH) and electrochemical conditioning. Glycine, lysine, histidine, serine, alanine, and aspartic acid were detected at copper macroelectrodes using cyclic voltammetry, with detection limits from 29 to 70 µM. Second, the results on copper nano-electrodes inside the cavities for detecting serine are discussed. A disadvantage of the devices in that their stability in the NaOH solution is limited. Electrochemical response in agitated solutions will also be addressed.

DL isomers of amino acids (99% purity) and sodium hydroxide (99.99% purity) were used as received from Sigma Chemical Company. Aqueous solutions were prepared with Milli-Q water (Millipore Inc.). A gold coin (Credit Suisse, 99.99%) and a chromium plated tungsten rod (R. D. Mathis) served as sources for thermal evaporation. Positive photoresist (AZ 4330) and photoresist developer (AZ 400K) were obtained from Hoechst-Celanese. For the copper macroelectrode experiments, the Ar was first humidified by passing it through a glass bubbler containing Milli-Q water, which prevented evaporation of the solution in the electrochemical cell during the experiments. A change in solution level will affect the submerged area of the electrodes, and consequently affect the electrochemical signal.

Copper Macroelectrodes

To make macroelectrodes, silicon wafers (0.35 mm) were covered with 50 Å of a chromium layer and 2000 Å of a copper layer using an Edwards 306 thermal evaporator. These were diced into pieces of ~6 mm×~20 mm. Prior to each experiment, a fresh electrode was rinsed with acetone (10–15 mL, 99.6% purity) and Milli-Q water (1 min under continuous flow, ~500 mL) then dried under a flow of argon. To obtain a stable response, each electrode was conditioned with a linear potential scan from −1200 mV to −1500 mV vs. Ag/AgCl (saturated KCl) for 10 min. The first cyclic voltammetry (CV) response in the alkaline amino acid solution that was obtained from −1500 mV to +1000 mV was used for quantitative determinations. The electrode area immersed in solution was calculated from measurements with calipers. For the reference electrode comparison tests, a copper wire was used as the working electrode. The wire was sanded with emery paper (3M, 320 grade) and rinsed with acetone and Milli-Q water prior to use.

Microcavity Electrodes

A five-layer cavity electrode system was constructed as described above with the exception that the second metal layer that forms the TNB electrode was made of copper, instead of gold. All experiments on amino acid oxidation at the microcavity electrodes were performed in the 50 µm diameter (8 µm deep) cavity and the TNB copper electrode (500 Å wide) served as the working electrode with an external Ag/AgCl (saturated KCl) reference and an auxiliary Pt flag electrodes.

Microcavity Electrode Fabrication Procedure

The following stepwise procedure was used to fabricate microcavities containing microelectrodes:

1. A 5" Si wafer was spin-coated with 4 µm of positive photoresist.

2. The photoresist (resist) was patterned with UV light to leave openings in the locations where the electrode leads would be located.

3. 25 Å Cr and 750 Å Au were deposited on the surface of the wafer by thermal evaporation.

4. The wafer was sonicated in acetone for 8–10 min to remove the resist, leaving only the pattern of the first layer.

5. The wafer was rinsed thoroughly with acetone and isopropyl alcohol to remove residue, followed by drying at 125° C. for 30 min.

6. The wafer was spin-coated with photodefineable polyimide (4 µm) and the entire layer was exposed to UV light.

7. The wafer was baked in a programmable oven at 150° C. for 30 min and 260° C. for 30 min.

8. After baking, 20 Å Cr and 500 Å Au were deposited on the surface by thermal evaporation.

9. The wafer was spin-coated with resist and the resist was patterned with the layer 3 mask.

10. The Au and Cr were etched in a 50% aqua regia solution (3 HCl: 1 $HNO_3$).

11. After rinsing, the wafer was dried for 30 min. before deposition of the polyimide.

For copper electrodes the alternative procedure was used for steps 8–11 as shown below.

8alt. After baking, the wafer was spin-coated with resist and the negative mask of layer 3 was used to pattern the resist.

9alt. 20 Å Cr, 800 Å Cu, and 15 Å Cr were deposited on the surface by the thermal evaporation.

10alt. The wafer was sonicated in acetone for 8–10 min to remove the resist and extra Cu.

11 alt. The wafer was rinsed thoroughly with acetone and isopropyl alcohol to remove residue before being dried for 30 min.

12. The wafer was spin-coated with 4 µm of polyimide and the entire film was exposed to UV light.

13. The wafer was baked using the procedure listed above as step 7.

14. 20 Å Cr and 1250 Å Au were deposited on the wafer by thermal evaporation.

15. The wafer was coated with resist and the resist patterned with the insulator layer mask.

16. The Au and Cr were etched with aqua regia as shown above.

17. After rinsing, the wafer was dried for at least 10 min.

18. Photoresist was deposited on the surface (6 µm) by spin-coating.

19. The soft cure was done at 90° C. in an oven for 20 min.

20. The resist was exposed to UV light for 23 s through the contact mask to pattern the cavity holes in the resist.

21. The coated wafer was hard baked at 125° C. for 20–30 min.

22. The top layer of Au was etched by Ar ion sputtering using the following conditions: 500 V bias, 30 mT pressure, 50 sccm flow rate. The total time for this etch was 7 min.

23. The top layer of polyimide was etched by reactive ion etching (RIE) using the following conditions: power=300 W, 300 mT pressure, 36 sccm $O_2$ flow, 4 sccm $SF_6$ flow. The total etch time was 10 min.

24. Layer 3 (either Cu or Au) was etched with Ar ion sputtering using the conditions listed above. The etch time was 2 min.

25. The bottom layer of polyimide was etched for 10 min using the above procedure.

26. The final step in the procedure was to dice the wafer leaving each chip as a separate functional system.

Electrochemistry

CV was performed in a Faraday cage with a BAS-100B, computer-interfaced potentiostat (Bioanalytical Systems). CV at the TNB electrodes in the microcavities and at the micropores for drop experiments involved a current amplifier (PA-1 pre-amplifier from BAS) between the cell and potentiostat. For the copper electrode experiments, a three-necked round bottom flask was used which provided a sealed environment in which oxygen presence could be minimized. Three different electrodes and an argon purge line were secured in feedthroughs with O-rings in the flask necks. All electrochemistry, except for the drop experiments, used a Ag/AgCl (saturated KCl) reference electrode and a platinum wire auxiliary electrode. The study of the stability of reference electrodes in 0.1 M NaOH solution compared Ag/AgCl (saturated KCl), Ag/AgI, Ag, and Au. The Ag/AgI reference electrodes were formed by electrochemical oxidization at a potential of +1.5 V vs. a Pt flag electrode of a silver wire in an electrolyte containing I—.

Using copper macroelectrodes, we:
determined electrochemical behavior for different electrolytes and pretreatments to optimized detection of amino acids
obtained sensitivity and detection limits for glycine, lysine, histidine, serine, alanine, and aspartic acid
evaluated stability of AgI reference electrode for possible use in microcavities Using copper microelectrodes, we:
compared sensitivities to those of the microelectrodes
investigated reproducibility from experiment to experiment and electrode to electrode
determined influence of convection on electrochemical responses Electrolyte Comparison and Method of Pretreatment for Macroelectrodes
Experimental
comparison of cyclic voltammetry in 0.1 M NaOH (aq) and 0.01 M NaOH (aq), with and without glycine (0.3 mM–1.0 mM)
pretreatment: rinsed each electrode with acetone and Milli Q water, promptly dried with flow of inert gas, and reduced the surface from −1.2 to −1.5 V vs. Ag/AgCl (sat'd KCl) for 10 min.

Summary of Results
The 0.1 M NaOH solutions gave a better response for glycine at the catalytic oxidation of copper
The 0.01 M NaOH solutions gave a better response for glycine at the complexation based oxidation of copper
The pretreatment allowed reproducible cyclic voltammetric responses Sensitivity and Detection Limits at Macroelectrodes
Experimental
cyclic voltammetry in 0.1 M NaOH (aq) with different concentrations of amino acids at 20 mV/s scan rate
the amino acids: alanine, aspartic acid, glycine, histidine, lysine, serine
the current at 688 mV was plotted against concentration to determine the sensitivity
the standard deviation of current at 688 mV in 0.1 M NaOH (aq) was used with the sensitivity to determine limits of detection Calculating the Limit of Detection $$Cm = \frac{k * Stdb}{m}$$

where
Cm=Limit of Detection,
k=constant=3,
Stdb=standard deviation of the blank solution, and
m=slope of current vs. concentration for the amino acid peak.

TABLE 7

Macroelectrode Detection Limits

| Amino Acid | Sensitivity/amp/cm$^2$/M | Limit of Detection/µm |
|---|---|---|
| Serine | −0.55 | 30 |
| Glycine | −0.4 | 41 |
| Lysine | −0.37 | 44 |
| Aspartic Acid | −0.26 | 63 |
| Histidine | −0.57 | 29 |
| Alanine | −0.24 | 69 |

Summary of Results
All amino acids exhibited similar cyclic voltammetry responses
The limits of detection for macroelectrodes were in the same range as those in the literature (30 to 70 µm)

Stability of Reference Electrodes
Experimental
Ag/AgCl (sat'd KCl), AgI, Au, and Ag reference electrodes were used in a solution under constant cycling for 30 min. to measure cyclic voltammogram responses [2 electrodes—one used as reference (gold) other used as working detector (copper)].

Summary of Results
reference electrodes exhibited drift from 20 mV to 57 mV over the 30 minutes time
worst behavior was for AgI
probably because of oxidation in NaOH solution
silver and gold reference electrodes, which are easier to make, would be the best choices as reference electrodes and will be used in the microcavity electrodes Expected Benefits of Microcavity Electrodes
  Smaller current leads to low iRu drop, allowing measurements in resistive media
  Small area leads to low capacitance allowing faster scan rates
  Small size, allowing measurements without significantly altering solution concentration
  Gold top layer helps protect sides of cavity (polyimide) during etching
  Gold disc on bottom of cavity is reference electrode, copper ban for detecting amino acids Effects of Turbulence on Gold Microcavity Electrodes
  Experimental
    detect 5 mM ruthenium hexamide (III) in 0.1 M $KNO_3$ with cyclic voltammetry in static and turbulent solutions at 10, 100, 500, 1000, and 100000 m V/s scan rates
    compare differences in peak currents for static and turbulent solutions at a 10 μm planar disc microelectrode, 50 μm disc microcavity electrode, and 50 μm diameter, 500 Angstroms wide ring microcavity electrode
    purge gas was bubbled through the solution to create turbulence
  Summary of preliminary results
    on plats of $i_{convection} - i_{static}$ (–i) vs. Scan Rate, the 50 μm microcavity disc electrode behaves similarly to the 10 μm planar electrode
    the 50 μm cavity does not protect the disk from convection
    we will investigate 10 μm and 5 μm diameter cavities in the future and expect to see a greater effect Detection of Amino Acids and Stability of the Copper Microcavity Electrodes
  Experimental
    perform cyclic voltammetry on copper microcavity electrodes in 0.1 M NaOH (aq) and in 0.1 M NaOH (aq) with varied concentrations f serine
  Summary of results
    the copper microcavity electrodes are not stable in the solutions tested
    electrodes could be used for single sue to acquire scans that were comparable to the macroelectrodes, but the current vs. concentration response was non-linear
    possible reasons for the failure of the electrodes could be
      NaOH reacts with the polyimide insulator
      high currents due to background and $0_2$ heat electrodes and cause separation at the interface with the polyimide Amino Acid Analysis at a Microcavity Device
  Fabrication of Copper Tubular Nanoband Electrodes. FIG. 4 illustrates the major steps involved in processing a cavity electrode device with three metal and two insulating layers. A similar system was reported previously, except the middle metal layer was Au, instead of Cu. The metal layer closest to the substrate has an electroactive region in the shape of a disk at the bottom of the cavity. This electrode was not used in the studies reported here. The geometry of the electroactive area of the Cu layer is that of a TNB around the walls of the cavity, with a length equal to the circumference of the cavity and a width equal to the thickness of the layer. Each metal layer is individually addressable through contact pads which are not shown in FIG. 4, but described in reference.

Results at Copper Macroelectrodes. Copper macroelectrodes were used to establish the best conditions for analysis of amino acids in alkaline solution. Those were then used as the initial conditions under which amino acid analysis was performed with the TNB copper electrodes in microcavities. The CV technique was chosen, not to achieve high sensitivity or low detection limits, but rather for its simplicity and diagnostic capability.

CV at Cu macroelectrodes in a solution of NaOH are similar to that reported by Baldwin and coworkers. The response exhibits anodic peaks at about –360 and –100 mV due to oxidation to Cu(I) and Cu(II) oxides, respectively. On the reverse sweep, two cathodic peaks appear at –490 mV and –790 that correspond to reduction back to Cu(I) and Cu(0), respectively. Two anodic peaks appear for the oxidation of amino acids: one at 200–400 mV due to the complexation mechanism and the other at 550–750 mV due to the catalytic mechanism.

The CV response to amino acids in alkaline solution is dependent upon NaOH concentration. The detection limit of glycine at the catalytic oxidation peak at a Cu macroelectrode in 0.01 M NaOH was 680 μM and in 0.1 M NaOH was 40 μM. Consequently, an electrolyte concentration of 0.1 M NaOH was chosen for our studies.

Changes in surface composition alter the electrochemical response of Cu electrodes to amino acids. Thus, the treatment of the Cu electrodes prior to analysis of amino acids is important. In work reported previously, Cu wire electrodes were rinsed with deionized water and electrochemically cycled until a stable CV response was obtained. When we followed this procedure with electrodes of thermally-evaporated copper on silicon substrates in 0.1 M NaOH, the magnitude of the peak current would increase with each electrochemical cycle, and did not appear to reach a stable response. The best way to obtain reproducibility from electrode to electrode for analysis of the same amino acid solution was to use the first CV response obtained after a preconditioning step. The preconditioning involved rinsing with acetone and water, and slowly ramping the potential at negative values from –1200 mV to –1500 mV for 10 min in the solution to be tested. We suspect that this reduces oxidized species on the surface, essentially normalizing the surface properties, before running CV to analyze for amino acids. When electrodes were stored in a polyethylene bag containing desiccant, this also greatly aided in the reproducibility, presumably because of the dry environment. CV of amino acid solutions at copper wire electrodes that were stored in air and preconditioned could be repeated multiple times with reproducible results. Copper-evaporated electrodes that were deposited one or more months prior to experiments and electrochemically pretreated in the same way gave reproducible data that were comparable to those of the copper wire. However, repetitive CV of amino acid solutions at recently deposited electrodes that were electrochemically pretreated in the same way exhibited consistent behavior over shorter time periods.

Sensitivity and detection limits for alanine, aspartic acid, glycine, histidine, lysine, and serine were determined by CV at 20 mV s$^{-1}$ using the catalytic peak current at 688 mV that was normalized to the area of the electrode in solution. Accurate values of electrode area in solution were difficult to obtain and lead to error in the determinations. (The microcavity electrodes have well-defined electroactive areas which should introduce less error.) Triplicate analyses, where each analysis involved a new electrode, were performed at 0.33 mM, 0.67 mM, and 1.0 mM of amino acid in 0.1 M NaOH. The linear least squares fit of plots of average current (mA cm$^{-2}$) vs. concentration (M) for each amino acid were usually within one standard deviation of the points. The calibration plot for histidine was the least linear. The resulting sensitivities were 0.24, 0.26, 0.40 0.57, 0.37, and 0.55 A cm$^{-2}$ M$^{-1}$, respectively. The detection limits were 69, 63, 41, 41 44, and 30 µM, respectively. Overall, the general trends in sensitivity and detection limits from one amino acid to another are similar to those reported in the literature.

Stability of Reference Electrodes. Future work in self-contained electrochemistry of amino acids in small volumes at the microcavity devices will require that one electrode serves as a reference. Thus, four reference electrodes were tested for stability in 0.1 M NaOH solution. The electrodes evaluated were Ag/AgCl (saturated KCl), Ag/AgI wire, Ag wire, and Au deposited on a silicon wafer. Continuous CV was performed for 30 min between −1500 mV and +1000 mV at a Cu wire electrode in 0.1 M NaOH. The absolute difference of peak potentials between the first and last cycles was added for all four peaks for a given electrode. The traditional Ag/AgCl (saturated KCl) reference demonstrated a shift of 40 mV. The Ag/AgI reference electrode was the least stable, with a potential shift of ~57 mV. This may be due to the growth of oxides (and perhaps loss of iodide) while the wire resides in alkaline solution. Once an oxide layer has formed on silver or gold in alkaline solution, the reference potential becomes stable. This may explain why the Ag and Au reference electrodes exhibited a smaller potential shift. Based on these results, either a Ag or Au electrode in the microcavity should serve well as a reference electrode for small volume analysis of amino acids.

Results at a Copper Nanoband Electrode in a Microcavity. Preliminary results are reported here for analysis of an amino acid with Cu TNB microcavity electrodes. Because serine gave the highest sensitivity and a linear response at the copper macroelectrodes, it was chosen as the test species for the TNB-microcavity electrodes. The faster scan rate was used to increase the signal at these small electrodes. The Cu(I) and Cu(II) anodic peaks are less well defined at the Cu TNB electrode, but overall, the shapes of the scans are similar to those obtained at the macroelectrodes. It was difficult to get highly reproducible results if measurements were taken from multiple scans at the same electrode, presumably due to chemical instability of the polyimide or polyimide/metal interfaces. Not enough data were taken to perform a statistical analysis, but there is clearly an increase of the catalytic peak with concentration. A linear least squares fit through the data yields a slope of 23 A cm$^{-1}$ M$^{-1}$. This value has been adjusted to a 20 mV s$^{-1}$ scan rate, for direct comparison to macroelectrode sensitivites, by dividing the nanoband current by five. (The current is proportional to the square root of scan rate.) Also, the area used to calculate this value is based upon the nominal dimensions of the cavity and thickness of the Cu layer. The resulting sensitivity is only a little less than half the sensitivity at the Cu macroelectrode.

EXAMPLE 6

Synthesis of micropore arrays containing two electrodes are reported for the first time. This configuration has several features different from the microcavity devices. These include a substrate that is flexible, an array of many pores (instead of one cavity), a greatly simplified fabrication procedure, and electrode-containing pores that are not blocked on either side to allow better access to solution and minimize buildup of electrochemical products. The micropores can contain two or more electrodes and are constructed from an insulating polymer sheet with pores having diameters from 70 to 30 µm. Characterization by cyclic voltammetry in 5 mM Ru(NH$_3$)$_6$$^{3+}$ and 0.5 M KNO$_3$ is carried out to show the electrochemical behavior of the electrodes. Multiple drop analysis demonstrates self-contained electrochemistry as an application of the device.

Aqueous solutions were prepared with Milli-Q water (Millipore Inc.). A gold coin (Credit Suisse, 99.99%) and a chromium plated tungsten rod (R. D. Mathis) served as sources for thermal evaporation. Positive photoresist (AZ 4330) and photoresist developer (AZ 400K) were obtained from Hoechst-Celanese. The polyimide sheet containing arrays of via holes that were formed using an excimer laser was a gift from Sheldahl, Inc. Solutions for electrochemical studies were purged 1 µm with UHP zero grade argon (Air Products Inc.) at least 10 min prior to analysis to minimize oxygen interference.

Micropore Electrodes

Construction of a three and four-layer micropore electrode system is reported for the first time. The substrate consists of a polyimide sheet, approximately 50 µm thick, containing an array of pores. The diameter of the pores where the laser entered the film is larger than the diameter on the exit side. The film was characterized with scanning electron microscopy (SEM) with a Hitachi S-2300 scanning electron microscope (25 kV accelerating voltage).

The polyimide film was cut to a workable size, put into a carrier made of cardboard with cut-outs to pattern the Au layer during deposition, and placed at a vertical angle in the thermal evaporator. A 50 Å Cr adhesion layer and a 1500 Å Au layer were deposited on one side of the polyimide film. At this steep angle, the inside walls of the pores are shielded from deposition. This prevents shorting through the pores to the metal layer that is subsequently deposited on the other side of the polyimide. The polyimide film was then flipped over and placed vertically so that 50 Å of Cr and 1500 Å of Au could be deposited on the other side through a comparable cardboard mask.

A 10 µm photoresist film was spin-coated onto the exit side of the Au/Cr/polyimide/Cr/Au film. The sample was then flipped over and exposed to UV light so that the bare Au side served as a mask and only the photoresist in the pores was exposed. Subsequent development opens the pores and leaves the photoresist film on the exit side unperturbed.

Electrochemistry

CV was performed in a Faraday cage with a BAS-100B, computer-interfaced potentiostat (Bioanalytical Systems). CV at the TNB electrodes in the microcavities and at the micropores for drop experiments involved a current amplifier (PA-1 pre-amplifier from BAS) between the cell and potentiostat. Micropore experiments were performed in an Ar-purged solution in an open beaker, with a positive pressure of Ar maintained over it. Drop experiments were performed in air. All electrochemistry, except for the drop experiments, used a Ag/AgCl (saturated KCl) reference electrode and a platinum wire auxiliary electrode.

Micropores

Physical Characterization of the Polyimide Sheet. The flexible polyimide sheet used as the base material for the micropore electrochemical devices hosts an array of holes that extends across the entire material. While forming a pore, the laser irradiates the entrance side of the sheet longer than the exit side, and thus, the resulting pore has a funnel shape. A film thickness of ~50 µm has been measured. The rim at the entrance side of the pore has an average diameter of 70

μm, but has some rough edges. The average diameter where the laser exits the film is about 30 μm. The rim on this side of the pore is much smoother. The pores are in a grid-like arrangement, yielding a density of about 400 pores cm$^{-2}$. An advantage of this film is that it is flexible and the pores have a high aspect ratio of depth-to-diameter without the great cost, steps, and time of microfabrication.

Fabrication of a Micropore Device. The layering of alternating materials of conductor and insulator was used to construct the micropore electrochemical devices. However, unlike the situation with the microcavity devices, the bare substrate starts with an array of holes. There are several advantages to this fabrication approach: (a) specially made masks are not required to define the holes, (b) wet and dry etching procedures are not needed to create the holes, (c) the metal layer on one side automatically serves as a mask for an insulating photoresist film deposited on the opposite side, and allows for exposing and clearing of photoresist from the holes. Although only three and four-layers are described and characterized here, the fabrication procedure should perform well for constructing devices with many more layers of materials.

Masks are needed, however, to pattern metal layers so that they can be individually addressed. These masks can be made from thin cardboard paper using a scalpel, and can define dimensions down to a few mm. The metal layer deposits onto the polyimide sheet in the shape of the pattern during thermal evaporation through the mask. The size of the patterns we report here for our initial studies have dimensions convenient for handling samples. The cut-out design consists of a rectangle of approximately 3 cm×4 cm, with a 1 cm×1 cm tab at the edge for making contact to the leads of a potentiostat. Also, the edges of the metal layer are confined inside the area of the polyimide (6 cm×6 cm) so that shorting to metal layers on the other side of the sheet is further minimized.

Electrochemical Characterization of Three- and Four-Layer Micropore Devices in Bulk Solution. Characterization of the electrochemical behavior of the micropore devices was carried out by CV in solutions of 0.5 M Ru(NH$_3$)$_6^{3-}$ and 0.5 M KNO$_3$. These studies indicate the quality of the fabrication and usefulness in electrochemical analyses. The potential difference between the anodic and cathodic peak current for the second electrode (exit side) is ~60 mV, indicating a one-electron reversible electron transfer. However, that for the first electrode (entrance side) is ~130 mV. It is not clear as to the cause of this response. The typical peak splitting for several three layer devices that were tested was about 80 mV. This response may be due to a poor connection to the contact tab or resistance in the gold film. The area of each electrode immersed in the solution was slightly different, and thus, the peak current is not the same for each. When the two electrodes are intentionally shorted together, a response approximately twice that of the individual electrodes is obtained. These results demonstrate that the electrodes are electrically insulated by the polyimide from each other and individually addressable.

In a four-layer device, a photoresist layer insulates one side of a gold layer (exit side) and polyimide insulates the other side. Thus, the only metal exposed is edge along the walls of the pore.

The geometry of the electroactive region of this gold layer is in the shape of an array of TNB electrodes. The CV response at 100 mV s$^{-1}$ in a solution of 0.5 M Ru(NH$_3$)$_6^{3+}$ and 0.5 M KNO$_3$ at a TNB electrode array in a four-layer micropore device is sigmoidal and characteristic of mass transport that is dominated by radial diffusion, which occurs at micro and nanoelectrodes when the diffusion layer is large relative to the size of the electrodes. To insure that the electrochemical response was coming from the nanoband electrodes and not from defects in the photoresist, CV was performed on a sample where the photoresist was left in the pores, which resulted in zero current. Consequently, the fabrication procedure easily produces large numbers of electrodes with nanoscopic dimensions that have a characteristic electrochemical response without mechanical polishing that can damage the edges, as has been used in the past to create band electrodes from layered materials. Quantitative analysis of the magnitude of the faradaic current and the charging current has not yet been performed on these initial data. A more controlled series of experiments are planned for the future to fully elucidate the quality of the seal between the insulators and electrodes, the reproducibility of the electrochemical responses, and to determine the actual area of the TNB electrodes exposed to the solution.

Microdrop Analysis with a Four Layer Micropore Device. An advantage of the design of the multilayer cavities and pores is that several electrodes lie within a few microns of each other. Thus electrochemical experiments can be performed easily on small samples placed on top of the device. Two or three electrodes present at or in the cavity or pore are enough to carry out self-contained electrochemical analysis without insertion of additional electrodes into the sample. Our previous experience with self-contained electrochemistry in small samples involved a device with a single microcavity and with one set of electrodes. This design works well for quantitation because the size of the electrodes are known and thus the current can be related to concentration of the redox species; also, the electrochemical response is independent of sample size, as long as the drop covers the cavity (~0.6 pL for a 10 μm diameter cavity). The limitation is that if a larger sample is available, there is no easy way to achieve a greater signal. The micropore array devices described here have a strength in this area. The larger the size of sample placed on the device, the larger the electrochemical response, because more pores are exposed to the solution. If quantitation is desired, then the area the sample covers on the device would need to be reproducible. Another advantage is the ability to place multiple samples on a common electrochemical cell, without chemical interference with each other.

We report preliminary work involving multiple drop analysis, demonstrating that the micropore devices are capable of self-contained electrochemistry. This experiment was performed on a four-layer device. The auxiliary and reference leads of the potentiostat were connected to the first electrode, which was the bare gold layer on the entrance side of the polyimide. The working lead was connected to the second gold layer, which was the array of TNB electrodes (exit side), having a much smaller total electroactive area. To block the solution from passing though the pores, the entrance side of the device was clamped to a microscope slide. Three 20 μl drops of a solution of 0.5 M Ru(NH$_3$)$_6^{3+}$ and 0.5 M KNO$_3$ were placed on the device sequentially, where CV was performed after the addition of each. The CV response is unlike the previous one. A possible reason for this difference is that the experiment was performed in air, instead of under a blanket of Ar, so that oxygen reduction can interfere with reduction of Ru(NH$_3$)$_6^{3+}$. However, as the number of drops increase, the current increases almost proportionally. This is because there are more TNB electrodes exposed to solution with each new drop. No precautions were taken to prevent evaporation of the solvent between CV runs, which will lead to some variation in the total current as the experiment progresses. To verify that the current is largely due to the presence of $Ru(NH_3)_6^{3+}$, the same experiment was carried out in pure electrolyte.

Whereas, the present invention has been described in relation to the drawings attached hereto, it should be understood that other and further modifications, apart from those shown or suggested herein, may be made within the spirit and scope of this invention.

What is claimed is:

1. An electrochemical sensing device wherein analyte-selective organic materials are suspended over a cavity, said cavity penetrating alternating submicroelectrode layers and insulating layers, said submicroelectrode layers having embedded electrodes in said cavity's walls, top opening and entire bottom of said cavity, and wherein said analyte selective organic materials being suspended such that they do not come in contact with the submicroelectrodes in the walls or bottom of the cavity.

2. A microcavity device comprising:
   (a) a flexible polymer substrate;
   (b) at least three integrated, independently addressable electrodes, wherein one of the electrodes is a disk electrode attached to an adhesion layer which is deposited on the substrate and covering the entire substrate and bottom of the microcavity and not used as a reference electrode, wherein at least one of the electrodes is nanoband or ring electrode embedded along walls of said microcavity, and wherein one of the electrodes is a ring electrode along the top opening of said microcavity;
   (c) conducting layers connected to said electrodes, said conducting layers being planar and parallel to one another and comprising contact pads;
   (d) an insulating layer separating adjacent conducting layers;
   (e) said conducting layers and insulating layer being on top of said substrate;
   (f) at least one microcavity penetrating said conducting layers and said insulating layer, said microcavity having a depth, a diameter and a top opening;
   (g) adhesion layers between the insulating and conducting layers and the conducting layer and the substrate;
   (h) said substrate comprising kapton, polydimethylsiloxane (PDMS), benzoclyclobutene (BCB), polymethylmethacrylate (PMMA), polyethylene terephthalate (PET), parylene, or polyimide; and
   (i) said insulating layers comprising polyimide kapton, or polydimethylsiloxane (PDMS).

3. The microcavity device of claim 2 wherein a thin film membrane covers said top opening.

4. The microcavity device of claim 3 wherein said membrane selectively permits mass transfer across said membrane.

5. The microcavity device of claim 3 wherein said membrane permits selective mass transfer of an analyte into said microcavity, selectively permits mass transfer of an analyte from said microcavity, and selectively prevents mass transfer of substances which are not analytes into said microcavity.

6. The microcavity device of claim 2 wherein said height of said microcavity is less than 1 millimeter.

7. The microcavity device of claim 2 wherein said diameter of said microcavity is less than 1 millimeter.

8. The microcavity device of claim 2 wherein a volume of said microcavity is between one femtoliter and one picoliter.

9. The microcavity device of claim 2, wherein said device includes a plurality of microcavities forming a multiple well array.

10. The microcavity device as recited in claim 9, wherein said array includes at least 96 wells.

11. The microcavity device of claim 2, wherein said microcavity device provides at least one electrochemical cell.

12. The microcavity device of claim 2, wherein said device is a recessed disk microelectrode.

13. A microcavity device comprising:
   (a) a rigid substrate;
   (b) at least three integrated, independently addressable electrodes, wherein one of the electrodes is a disk electrode attached to an adhesion layer which is deposited on the substrate and covering the entire bottom of the microcavity and not used as a reference electrode, wherein at least one of the electrodes is nanoband or ring electrode embedded along walls of said microcavity, and wherein one of the electrodes is a ring electrode along the top opening of said microcavity;
   (c) conducting layers connected to said electrodes, said conducting layers being planar and parallel to one another and comprising contact pads;
   (d) an insulating layer separating adjacent conducting layers;
   (e) said conducting layers and insulating layer being on top of said substrate;
   (f) at least one microcavity penetrating said conducting layers and said insulating layer, said microcavity having a depth, a diameter and a top opening;
   (g) adhesion layers between the insulating and conducting layers and the conducting layer and the substrate;
   (h) said substrate comprising silicon wafer, glass, mica or ceramics; and
   (i) said insulating layers comprising polyimide, kapton or polydimethylsiloxane (PDMS).

14. The microcavity device as recited in claim 13, further comprising:
   (i) a thin film membrane covering said top opening; and
   (ii) wherein said membrane selectively permits mass transfer across said membrane.

15. The microcavity device of claim 14 wherein said membrane permits selective mass transfer of an analyte into said microcavity, selectively permits mass transfer of an analyte from said microcavity, and selectively prevents mass transfer of substances which are not analytes into said microcavity.

16. The microcavity device of claim 13 wherein said depth of said microcavity is less than one millimeter.

17. The microcavity device of claim 13 wherein said diameter of said microcavity is less than one millimeter.

18. The microcavity device of claim 13 wherein said electrodes are selected from a group consisting of band electrodes and disk electrodes.

19. The microcavity device of claim 13 wherein there are at least two electrodes.

20. The microcavity device of claim 13 wherein the volume of said microcavity is between one femtoliter and one picoliter.

21. The microcavity device of claim 13 wherein said device includes a plurality of micro-cavities forming a multiple well array.

22. The microcavity device of claim 21 wherein said array includes at least 96 wells.

23. The microcavity device of claim 13 wherein said device is a recessed disk microelectrode.

24. A microcavity device for detecting amino acids, comprising:
   (a) a silicon wafer to act as a substrate for the microcavity device;
   (b) conductor layers;
   (c) electrodes connected to said conductor layers, wherein one of the electrodes is a microdisk electrode on the substrate and covering the bottom of the microcavity and not used as a reference electrode;
   (d) a polyimide insulating layer to separate said conductor layers; and
   (e) a microcavity penetrating at least one electrode and at least one insulating layer, wherein said conductor layers and said electrodes are made of at least one of gold and copper.

25. The microcavity device of claim 24 wherein a thin film membrane covers said microcavity.

26. The microcavity device of claim 25 wherein said membrane permits selective mass transfer of an analyte into said microcavity, selectively permits mass transfer of an analyte from said microcavity, and selectively prevents mass transfer of substances which are not analytes into said microcavity.

27. The microcavity device of claim 24 wherein said microcavity further comprises a depth and a diameter and wherein said depth of said microcavity is less than one millimeter.

28. The microcavity device of claim 27 wherein said diameter of said microcavity is less than one millimeter.

29. The microcavity device of claim 24 wherein said electrodes are selected from a group consisting of band electrodes and disk electrodes.

30. The microcavity device of claim 24 wherein there are at least two electrodes.

31. The microcavity device of claim 24 wherein the volume of said microcavity is between one femtoliter and one picoliter.

32. The microcavity device of claim 24 wherein said device includes a plurality of micro-cavities forming a multiple well array.

33. The microcavity device of claim 32 wherein said array includes at least 96 wells.

34. The microcavity device of claim 24 wherein said microcavity device provides at least one electrochemical cell.

35. The microcavity device of claim 32 wherein said device is a recessed disk micro-electrode.

* * * * *